(12) United States Patent
Eastman

(10) Patent No.: US 10,096,384 B2
(45) Date of Patent: Oct. 9, 2018

(54) ARTIFICIAL INTELLIGENCE EXPERT SYSTEM

(71) Applicant: Disco Health, LLC, Jackson, WY (US)

(72) Inventor: John W. Eastman, Jackson, WY (US)

(73) Assignee: DISCO HEALTH, LLC, Jackson, WY (US)

( * ) Notice: Subject to any disclaimer, the term of this patent is extended or adjusted under 35 U.S.C. 154(b) by 0 days.

(21) Appl. No.: 15/843,813

(22) Filed: Dec. 15, 2017

(65) Prior Publication Data

US 2018/0174684 A1 Jun. 21, 2018

Related U.S. Application Data

(60) Provisional application No. 62/437,203, filed on Dec. 21, 2016.

(51) Int. Cl.
*G16H 50/20* (2018.01)
*G06N 99/00* (2010.01)
*G16H 10/60* (2018.01)

(52) U.S. Cl.
CPC .......... *G16H 50/20* (2018.01); *G06N 99/005* (2013.01); *G16H 10/60* (2018.01)

(58) Field of Classification Search
None
See application file for complete search history.

(56) References Cited

U.S. PATENT DOCUMENTS

| | | |
|---|---|---|
| 2013/0325856 A1 | 12/2013 | Soto Matamala et al. |
| 2014/0344103 A1 | 11/2014 | Zhu et al. |
| 2016/0004394 A1 | 1/2016 | Macadaan et al. |
| 2016/0132953 A1 | 5/2016 | Davar et al. |
| 2016/0294663 A1 | 10/2016 | Veres et al. |
| 2017/0323196 A1 | 11/2017 | Gibson et al. |
| 2017/0330069 A1 | 11/2017 | Liu |

OTHER PUBLICATIONS

Pri-Med Uses Patient Panel Data to Create Precision CME™, Pri-Med LLC, dated Sep. 15, 2015.
Krames on FHIR, The StayWell Company, LLC, 2017.

*Primary Examiner* — Valerie Lubin
(74) *Attorney, Agent, or Firm* — Knobbe, Martens, Olson & Bear LLP

(57) ABSTRACT

Systems and methods are disclosed that access over a network a set of codes and respective code descriptions from a first data store. Course data for courses is accessed over a network from a second data store. Code descriptions and course data are compared, and the comparison is used to generate a mapping of courses to codes. The network interface is used to access codes associated with patient records for a plurality of patients from an electronic medical record system associated with a medical service provider. Relevancy values are calculated for codes using the codes associated with patient records. The calculated relevancy values and the accessed mapping of courses to codes are used to generate a first ranked presentation of recommended courses. A course selection is detected. Using the selection, a second ranked presentation of recommended courses is generated by a learning engine with updated learning engine weights.

23 Claims, 28 Drawing Sheets

JOHN SMITH, MD EMR - CME VIEW

| PATIENT | LABS | eRx | LIBRARY | CME | CLINIC | OFFICE | SETTING |

AMERICAN HEART PROCEDURES ANNUAL MEETING
DALLAS, TEXAS           FACULTY: RICHARD S. TELLER MD                    7 CREDITS
COURSE ABSTRACT                   STANFORD CARDIOLOGY
                                  MARY LANG MD                           (REGISTER)
                                  U. CALIFORNIA SAN FRANCISCO

MEETINGS

1. AMA HYPERTENTION TODAY - MIAMI
2. ACOG WINTER MEETING - SEATTLE
3. AMERICAN HEART PROCEDURES - DALLAS
4. CARDIOLOGY WORKING GROUP - CHICAGO

ARTICLES

1. FLORI NOVE HAVIN SEMP LAK SOA
2. FLORI NOVE HAVIN SEMP LAK SOB
3. FLORI NOVE HAVIN SEMP LAK SOC
4. FLORI NOVE HAVIN SEMP LAK SOD

WEBINARS

1. MUS LATEM NOREMUS A
2. MUS LATEM NOREMUS B
3. MUS LATEM NOREMUS C
4. MUS LATEM NOREMUS D

PREFERENCE PICKS

1. AMERICAN HEART PROCEDINGS - DALLAS
2. FLORI NOJE HAVIN SEMP LAK SO B
3. CORDIOLOGY WORKING GROUP - CHICAGO
4. MUS LATEM NORE MUS D

DR. JOHN SMITH          PREFERENCES      (TRACK)   CME CREDITS TO DATE         10
NPI. 12345678           PRACTICE PROFILE           CME CREDITS REQUIRED        15
                                                   CME DEAD LINE      JUNE 5, 2017

JOHN SMITH EMR - PATIENT RECOMMENDED PROGRAMS
- FROM LINK ON PATIENT TAB: PATIENT EDUCATION -

MARY JONES
123 - 47 - 1234

PROBLEM LIST
˅ ˅ ˅

PROBLEM LIST
˅ ˅

LAB TESTS/RESULTS
˅ ˅ ˅ ˅ ˅ ˅

PREFERRED DELIVERY

☐ USPS     ☐ TEXT MESSAGE
☒ EMAIL    ☐ PRINT

RECOMMENDED PROGRAMS

☐ DIABETIC & YOU (WEBSITE)
☐ DEALING WITH PAIN (WEBSITE)
☐ MY HEART (MOBILE APP)
☐ LEARNING HYPERTENSION (ARTICLE)

[SUBMIT]

JOHN SMITH MD - PREFERENCES

DR. JOHN SMITH

NPI. 12345678

AUTHORIZED ORGANIZATIONS
- CAL MEDICAL SOCIETY
- AM COLLEGE CLINICAL ONCOLOGY
- AM MEDICAL ASS'N (REPORT)  (ADD)

SHOW MEETINGS IN...
- MIAMI ⇨
- SEATTLE ⇨
- ADD CITY... ⇨

SHOW TOPICS ON...
- HYPERTENTION ⇨
- GERD ⇨

SHOW COURSES MATCHING...
- NDC 7474747462 ⇨
- CPT ZI124049 ⇨

SHOW AUTHORS/SPEAKERS
- ROBERT TELLER MD ⇨
- ADD PERSON ⇨

SHOW PROCEDURES ON...
- CARDIO PLANOSCOPY ⇨
- ADD PROCEDURE ⇨

FIG. 12

Courses for John Smith MD

Date | Location | Cost

| Title | Cost | Location | Relevance | Dates |
|---|---|---|---|---|
| Osteoporosis Essentials for Clinicians | $139 | Memphis, Tennessee | 5.211291117 | 2015-10-24 to 2015-10-24 |
| Osteoporosis Essentials for Clinicians | $139 | Pittsburgh, Pennsylvania | 5.211291117 | 2015-11-21 to 2015-11-22 |
| Fall 2015 Clinical Vaccinology Course | $755 | Bethesda, Maryland | 3.858389235998938 | 2015-11-13 to 2015-11-13 |
| Can Red Wine Cut Cardiometabolic Risk Factors in Diabetes? | $0 | online | 3.519468656 | 2015-11-11 to 2016-11-11 |
| Update on Benign and Malignant Hepatobiliary and Pancreatic Disease | $675 | Seattle, Washington | 3.122235098 | 2015-10-23 to 2015-10-24 |
| Patient Encounters in Multiple Sclerosis: Monitoring and Assessment | $0 | online | 3.086451079 | 2015-08-26 to 2016-08-26 |
| Assessing Collaborative Skills in Customized CLL Management | $0 | online | 2.983631855 | 2015-10-30 to 2016-10-30 |
| Cases in Echocardiography, Cardiac CT, and MRI | $749 | Napa, California | 2.985985657 | 2015-10-21 to 2015-10-24 |
| Internal Medicine Update | $675 | Quintana Roo, Mexico | 2.859584732 | 2016-03-17 to 2016-03-19 |
| From the 2015 Conferences to the Clinic: Latest Evidence Updates in MDD and Anxiety Disorders | $0 | online | 2.812465698 | 2015-08-20 to 2016-08-20 |

FIG. 13

Osteoporosis Essentials for Clinicians

Practice Type:
Any

Activity type:
Live

Location:
Memphis, Tennessee, 2015-10-24 – 2015-10-24

Credits:
12.25

Cost:
139

Description:
The core elements of this program provide a set of standard practices and information to raise the level of awareness and education in bone densitometry and osteoporosis. The course is offered in two parts. The first day is for those engaged specifically in the performance and interpretation of DXA scans. It also is offered in combination with a subsequent Day 2 which focusses on the prevention, treatment and management of osteoporosis. Individuals may register for only Day 1 or for Day 1 and Day 2.

Provided by:
Other

Commercially sponsored:
true http://www.iscd.org/event/memphis-tn-osteoporosis-essentials-for-clinicians/

FIG.18

Chronic HCV Infection: Treating Unique Patient Populations

Practice Type:
Any

Activity type:
Knowledge and Practice

Location:
online, 2015-08-20 till 2016-08-20

Credits:
0.25

Cost:
0

Description:
This activity is intended for gastroenterologists, infectious diseases/HIV specialists, hepatologists, primary care physicians, and other healthcare professionals. The goals of this activity are to improve initial and ongoing patient assessments among patients with a diagnosis of chronic HCV, and increase timely and appropriate treatment initiation among patients for whom treatment is indicated.

Provided by:
MEDSCAPE

Commercially sponsored:
true http://www.medscape.org/viewarticle/840693

Practice List

- Any
- pediatrician
- orthopaedist
- radiologist
- surgeon
- Family Practitioner
- primary care physician
- oncologist
- anesthetist
- Cardiologist
- allergist
- Dermatologist

FIG. 22

ARTIFICIAL INTELLIGENCE EXPERT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention is related to content selection and access.

Description of the Related Art

An expert system may be configured to solve complex problems in a particular domain by reasoning about knowledge. An expert system typically includes an inference engine, a knowledge base, and a user interface. The knowledge base may include domain specific knowledge, facts and rules. The inference engine may apply the rules to the known facts to deduce new facts and provide solutions.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An aspect of the disclosure relates to systems and methods that access over a network a set of codes and respective code descriptions from a first data store. Course data for courses is accessed over a network from a second data store. Code descriptions and course data are compared, and the comparison is used to generate a mapping of courses to codes. The network interface is used to access codes associated with patient records for a plurality of patients from an electronic medical record system associated with a medical service provider. Relevancy values are calculated for codes using the codes associated with patient records. The calculated relevancy values and the accessed mapping of courses to codes are used to generate a first ranked presentation of recommended courses. A course selection is detected. Optionally, using the selection, a second ranked presentation of recommended courses is generated by a learning engine with updated learning engine weights.

An aspect of the disclosure relates to systems and methods that access over a network a set of codes and respective code descriptions from a first data store. Course data for courses is accessed over a network from a second data store. Code descriptions and course data are compared, and the comparison is used to generate a mapping of courses to codes. The network interface is used to access codes associated with records for a plurality of entities from a record system associated with a service provider. Relevancy values are calculated for codes using the codes associated with the records. The calculated relevancy values and the accessed mapping of courses to codes are used to generate a first presentation of recommended courses. A course selection is detected. Optionally, using the selection, a ranked presentation of recommended courses is generated by a learning engine with updated learning engine weights.

BRIEF DESCRIPTION OF THE DRAWINGS

FIGS. 2-6 illustrate example processes.
FIGS. 7-27 illustrate example user interfaces.
While each of the drawing figures illustrates a particular aspect for purposes of illustrating a clear example, other embodiments may omit, add to, reorder, and/or modify any of the elements shown in the drawing figures. For purposes of illustrating clear examples, one or more figures may be described with reference to one or more other figures, but using the particular arrangement illustrated in the one or more other figures is not required in other embodiments.

DETAILED DESCRIPTION

Figure 1A:
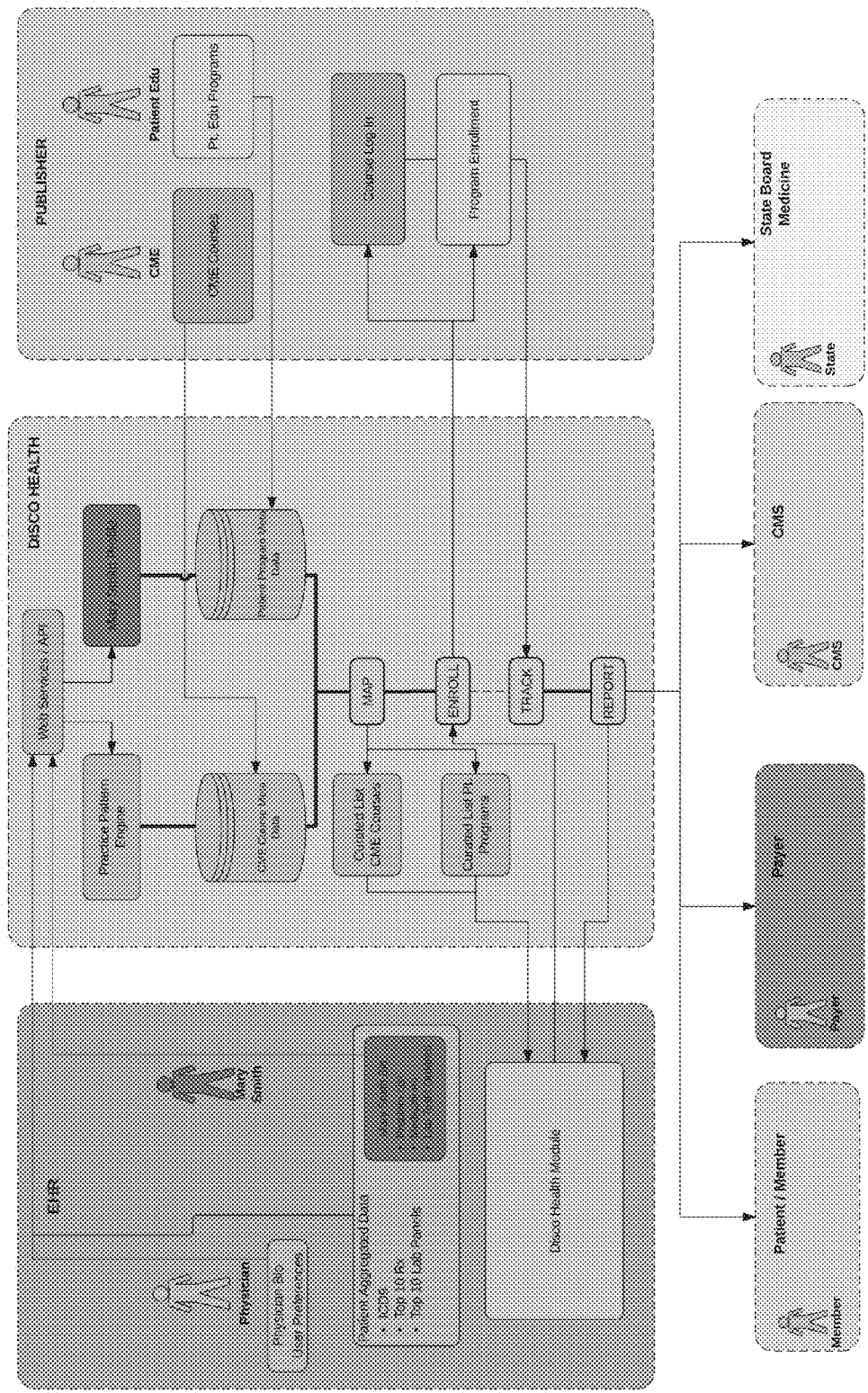
FIG. 1A illustrates an example architecture.

An aspect of this disclosure relates to technology solutions for a comprehensive system to securely, seamlessly, and transparently connect users with content. An aspect of this disclosure relates to an optional learning engine that generates recommendation for users having different functions and interests utilizing information obtained or inferred from electronic records systems.

For example, the users may include hospitals, payers, medical directors, pharmaceutical companies, disease management companies, physicians, patients, and content providers, and the electronic records systems may include an electronic health record (EHR) system and/or a patient health portal. By way of further example, the content provided by content providers may include continuing medical education (CME) courses, continuation legal education (CLE), Continuing Professional Education (CPE) courses, Massive Open Online Courses (MOOC), or the like.

Optionally, an artificial intelligence engine may be utilized that identifies and selects content, such as CME courses, from one or more content providers for a user, such as a doctor or other medical professional, from patient data and/or other data in associated electronic records, such as EMR (electronic medical records). The selected courses (which may include meetings and conventions that present educational material) may be presented as a curated list of education courses that may optionally be unique to that user or unique to a set of users having similar characteristics.

By way of further example, the user may be a patient. A artificial intelligence engine may be utilized that identifies and selects, for the patient, patient education content from one or more content providers, from data associated with the patient. For example, the patient data may include a patient problem or complaint list, patient medications, patient lab test results, scheduled patient lab tests, previously and/or future scheduled appointments with physicians, and/or other data. The identified patient education content may be identified and/or presented to the patient during an appointment or other encounter with a medical service provider.

A recommendation system, which may include the learning engine, may provide an ecosystem for recurring education directives that enables web-based implementations, app based implementations, software tools for course enrollment, control and administration, and opportunities for additional services and revenues.

To provide background as to the need to find a technological solution to provide an efficient technique for identifying content suitable for a user, the 2015 professional medical education market is estimated to have encompassed 26 million course interactions between physicians and other health care professionals with CME courses. During this period of time, medical education publishers invested an estimated $2.4 B to produce and deliver CME courses. In addition, patient education programs created for the millions of patients that access the healthcare network are expected to increase with the implementation of the Centers for Medicare & Medicaid Services (CMS) "meaningful-use" criteria (mandating patient education connectivity at the point-of-care).

However, conventional approaches fail to deliver such content utilizing EMR systems (sometimes referred to as EHR systems) or patient portals, and fail to provide an adequate tool to generate a custom course list for a medical service provider based at least in part on the provider's EMR patient population data. The conventional approach has the physician seeking out required CME from various sources of print and digital material in a time consuming, scattershot approach. The recommendation system disclosed herein offers solutions to create a distribution channel for education materials that are personalized for that physician and optionally delivered through their EMR. Conventionally, the medical provider's adoption of EMR workflow is in place, but an EMR embedded solution for distribution of education is lacking.

Thus, aspects of the disclosure relate to the surprising, unexpected, and unconventional use of EMR systems and user interfaces to provide access to personalized education content for medical service providers and/or patients. Further, the use of EMR systems and user interfaces provides an efficient channel to provide access to educational content recommendations, as medical service provides spend an increasing amount of time in front of such EMR user interfaces during their clinical work day.

Increasingly, access to clinical professionals during their office hours has become more limited. As more patients enter the healthcare system and as reimbursement models are focusing more on value and less on volume, doctors are ever more time constrained. Medical providers' engagement with EMR systems has increased to the point where some medical providers may spend more time in front of an EMR system display than they spend with their patients.

Publishers (or other providers) of CME courses, live meetings, or webinars would benefit from content distribution channels that reach a suitable practicing physician.

The physician's EMR system is where their patient data "lives," and so the provider's practice routine and their point-of-care encounter with their patient is today closely tied to the provider's access to their EMR. An aspect of the disclosure relates to a recommendation system that uses the EMR data to build a custom list of patient education programs for the medical provider. These targeted patient programs are optionally presented to the provider on the EMR screen during the patient encounter and/or to the patient via a patient portal user interface.

The recommendation system may execute or participate in processes, including mapping processes, enrollment processes, tracking processes, and/or reporting processes.

The delivery and recommendation of education material to other professionals with similar regulatory reporting requirements or education needs in the fields of law, accounting, engineering, pharmacy, and/or the like may also be provided using the systems and processes described herein. However, for the sake of clarity, the examples herein illustrate the application of the system to the recommendation of medical service provider courses and patient programs.

A variety of sets of codes have been developed to normalize and standardize medical nomenclature. A mapping process may map such codes to education content. The codes and code mapping may be used in selecting and/or recommending content. For example, some or all of the following codes and/or other codes may be analyzed and mapped to medical educational content (e.g., CME courses, live meetings, webinars, etc.):

ICD10 (International Classification of Disease);
CPT (Current Procedural Terminology);
MESH—Medical subject headings a standardized vocabulary for medical subjects;
NDC (National Drug Code);
HCPCS (Healthcare Common Procedure Codes which may be used with CPT (Current Procedural Terminology) codes to describe services outside of a physician's office);
LOINC (Logical Observation Identifiers Names and Code);
SNOWMED (Systematized Nomenclature of Medicine which provides codes, terms, synonyms and definitions which cover anatomy, diseases, findings, procedures, and the like).

An illustrative example of the mapping process in the context of CME courses will now be described.

Physician-EHR interactions may be captured by a code or set of codes. For example, when the patient comes in for a physician appointment with a fever and rash, an initial diagnosis may be made of the patient's condition, and the encounter may be captured using one or more codes, such as one or more of the approximately 70,000 ICD10 (International Classification of Disease) codes. To confirm the diagnosis, the patient's blood may be drawn and a lab test may be run on the blood specimen, which may be captured in one or more of approximately LOINC (Logical Observation Identifiers Names and Code) codes. To confirm the diagnosis, the physician may order an abscess be removed and pathology completed on tissue around the rash, which may be captured using one or more of approximately 68,000 CPT (Current Procedural Terminology) codes. To relieve the pain and rash, the physician may order a drug, which is captured using one or more of approximately 100,000 NDC (National Drug Code) codes.

A relation may be determined between a given CME course and one or more of the foregoing codes and/or other codes. By way of illustrative example, a course about Lyme disease may be linked to corresponding codes for diagnosis, lab testing and drug therapy for Lyme disease. Disadvantageously, conventional systems fail provide a map between such codes and CME courses. By contrast, an aspect of this disclosure provides a mapping of codes with course content, which may be utilized to select and recommend courses to medical service providers and patients. Thus, with such a map, courses may be selected and targeted to a physician or other consumer of educational material based on the consumer's clinical practice patterns, providing value to such educational material consumer, as well as to publishers of such educational material whose content is more accurately targeted. As part of the mapping process, course identifiers may be stored in association with one or clinical codes, thereby tagging the course with relevant codes.

Once a course is tagged with clinical codes, the course can be matched with a physician through the physician's EMR patient data set. For example, if the physician has a number of patients with Lyme Disease, then the diagnosis code(s), lab code(s), and drug code(s) associated with Lyme Disease will be prevalent in the EMR data for the physician's patients. The physician's EMR patient data set may be searched, and each code may be enumerated. Optionally, the enumeration may be limited to a specified time period, such as the previous 24 or 48 months to better identify the types of diseases or other medical condition's the physician is currently treating. Using the enumeration of codes, it may be determined that the physician's practice involves treatment of Lyme Disease, and so courses about Lyme Disease may then be selected and corresponding recommendations presented to the physician as these courses are targeted to the physician's practice profile.

The process of building a targeted list of CME courses for a physician may be performed using some or all of the states discussed below. More detail on the example process is described with reference to FIG. 1A. The process may be performed using the disclosed recommendation system. The distributed network system better ensures that up to date course and program information is utilized by the recommendation system. Further, the distributed network system may reduce the hardware resources that would otherwise be needed by the recommendation system.

The recommendation system may tag courses with codes. For example, the system may perform a free text keyword search of course-related data (e.g., course title, abstract, summary, tags, content of the course itself, etc.) and of code-related information, perform comparisons, and identify matches. If course data is identified that matches code-related information, an association between the corresponding course and code may be stored to provide a course-to-code mapping. By way of illustrative example, a course abstract or other related course text may be accessed and, in addition, code descriptions may be accessed that describe the code and its clinical context (e.g., code 250.20 may be associated with the description: "Diabetes with hyperosmolarity, type II or unspecified type, not stated as uncontrolled"). The process may attempt to find keyword matches between the course abstract or other related course text, and the code descriptions.

Optionally, machine learning is utilized to aid in the generation of course recommendations. For example, machine learning may be used to observe the physician-course selection relationships in order to create analytics that can be used to recommend additional courses to that physician.

By way of illustration, an artificial intelligence engine employing machine learning may be utilized to determine an optimum or enhanced recommendation of courses for content consumers. For example, the artificial intelligence engine may vary course recommendations made to similar consumers (e.g., physicians with the same or similar practice profiles) and learn which recommendations for a given practice profile-type tends to result in the highest likelihood that the consumer (e.g., physician) will select and consume the recommended course content.

The inputs to the learning engine may include some or all of the historical access of content from a given user or set of users (e.g., those physicians with similar practice profiles). The artificial intelligence engine may be configured to identify correlations between the input information and the user's historical responses to course recommendations (e.g., clicks on link to recommended courses to view additional information regarding the recommended courses, purchases of recommended courses, actual consumption of recommended courses (e.g., view of a course video file, reading of a course document, etc.), etc.). The correlations may then be used in performing predictive analytics to determine how a user will respond to various future course recommendations.

The learning engine may comprise a neural network. The neural network may include one or more convolutional layers, pooling layers and fully connected layers. The neural network may include one or more layers of one or more nodes. A given node may input one or more items of information, such as a user's historical responses to course recommendations (e.g., clicks on link to recommended courses to view additional information regarding the recommended courses, purchases of recommended courses, actual consumption of recommended courses (e.g., view of a course video file, reading of a course document, etc.), etc.). The node may differently weight various inputs. The weighted inputs may be summed and a function may be applied to the summed weighted inputs to generate a prediction as to a user's response to a given course recommendation. The prediction may be compared to the user's actual historical response. If there is a difference, the difference constitutes a prediction error. The weights may be adjusted using back propagation, and the prediction may be performed again to determine if the error has decreased or increased. The weights may be repeatedly adjusted until the error cannot be reduced any further. A gradient descent process may be utilized to reduce the error.

As will be described, a physician's profile may be mapped to one or more courses. For example, a physician's profile may be generated by accessing and examining the physician's patient population data set that dynamically exists in the physician's EMR dataset. For example, the system may compile profiles of the physician's patient demographics (e.g., age, gender, residential address, profession, income, etc.). In addition, the system may parse the patient codes and determine i) volume of codes; ii) frequency of a given unique code; and/or iii) the respective dates when the codes were added to the EMR dataset. Other code related data may be examined as well (e.g., volume and/or frequency of codes for each library of code (ICD10, MESH, CPT, NDC, HCPCS, LOINC, SNOWMED, etc.)).

The variables of volume, frequency and/or date (where the variables may be assigned different weights) are then used to calculate for a relevance value for a given code, where the relevance value may be based on a combination of the weighted values of each variable. By way of illustrative example, Code 123 may have a quantity of occurrences in the physician's EMR that is greater than the quantity of occurrences for Code 456, and therefore the process may determine that Code 123 has a higher relevance score based on volume. By way of further illustrative example, Code 789 might have been recorded into the physician's EMR with a higher frequency value over a recent time period (e.g., over a specified time period, such as the last 6 months, last 12 months, last 24 months, or other specified time period) and thus be assigned a higher relevance score than Code 012 which may have the same frequency value overall, but a lower frequency value over the specified recent time period (e.g., where Code 012 may not have been logged into the EMR over the past 24 months).

The code relevance score may optionally be calculated using the following example formula:

$$\text{Relevance value} = Wv_1 \, f_v(\text{Volume})_{tp1} + \ldots + Wv_n f_v(\text{Volume})_{tpn} + W_{f1} f_f(\text{Frequency})_{tp1} + \ldots + Wt_{fn} f_f(\text{Frequency})_{tpn}$$

Where:
- $Wv_1$ is the volume weight for time period 1 (tp1)
- $Wv_n$ is the volume weight for time period n (tpn)
- $f_v$ is a volume function
- $W_{f1}$ is the frequency weight for time period 1 (tp1)
- $W_{vn}$ is the frequency weight for time period n (tpn)
- $f_f$ is a frequency function The calculated relevancy scores for corresponding codes may be ranked. For example, rankings can be generated for one or more of the following codes: ICD10, MESH, CPT, NDC, HCPCS, LOINC, SNOWMED, and/or other codes. Optionally, codes satisfying certain criteria (e.g., ranked within the top codes, such as within a threshold of the top ranked code (e.g., top 10, top 20, top 30, etc.)) may be identified and selected to define/represent the physician's practice profile. Optionally, the code rankings and/or relevancy scores may also be used to detect recent trends in which codes are added to the physician's EMR to identify current clinical encounters that indicate the physician's contemporary practice pattern. Optionally, the code rankings and/or relevancy scores for multiple physicians within a defined geographical area or across multiple geographical areas may be used to identify an increase or decrease in a health state or condition (e.g., a disease, obesity, accidents, etc.) across large populations of patients.

Optionally, the recommendation system is architected to be agnostic as to which EMR vendor chooses to offer the physician access to the curated list of CME courses. APIs are optionally provided that enable the system software to access and input EMR data and physician practice profile data and generate and return a curated list of recommended courses to the EMR vendor for presentation to physicians within the vendor's EMR user interfaces (UI)/user experiences (UX).

Thus, the recommendation system may run a database, mapping courses to codes, against the codes from the physician's practice profile to build a customized list of matching CME courses which may be unique to that physician. As will be described, the customized list of matching CME courses may be further refined.

The system may score each course-profile match and generate a relevance score for a given match. The system may optionally the list of matching courses using the corresponding relevance scores.

Physicians can aid in the increase in course recommendation accuracy by adding preferences. For example, optionally, the relevance score may be calculated using preferences expressly submitted by a user, such as a physician. By way of illustration, a user preference interface, such as at that illustrated in FIG. 9, may be provided for display on a user's terminal that enables the user to specific preferences for course subject matter, publication date range for course, course presentation type (e.g., in person, live over a network, downloadable video/audio, audio-only, audio and printed materials, text/still images, etc.). The specified user preferences may then be stored in a corresponding user record for later use in generating course recommendations.

By way of illustrative example a user interface may be provided that enables physician to indicate a preference for courses that focus on a specific procedure code or drug code as a way to improve the physician's clinical competency. The user interface may further enable the user to specify a preferred location for live courses. For example, the user interface may indicate a preference for live courses located in San Francisco, Calif. The user interface may further enable the user to specify a preferred presenter, a preferred course provider, a preference for one or more course types (e.g., a video course, a text (article), a webinar course, live courses, downloaded courses, streamed courses, courses accessed via a dedicated or non-dedicated phone application, computer application, etc.), a preference for a course length (e.g., 30 minutes, 1 hour, etc.), a preference for amount of learning credits received, a preferred maximum course price, a preferred minimum course price, etc.

By filtering course recommendations based on user preferences and the codes associated with the courses, the search process for courses to recommend is reduced, and the needed processing power is likewise reduced. Further, the speed associated with identifying courses to recommend is increased. In addition, the recommendation system may eliminate courses from consideration if those courses fall below a determined search relevance value (or threshold) generated by the system generates. The process for generating relevance values for course selection is discussed in greater detail elsewhere herein.

Thus, as similarly described elsewhere herein, the system may perform some or all of the following:
- map clinical codes to education courses for a consumer (e.g., physician);
- create a new or enhanced course record (a 'smart' course record) as the result of the course being defined by relevant clinical codes;
- build a physician practice profile (e.g., by evaluating the top or higher ranked codes in the physician's EMR by volume, code frequency, based on when codes were entered into the EMR, and/or code trending data).

As discussed elsewhere herein, a relevancy value may be generated from the evaluation that is specific to that course-code relationship, and the relevancy value may be used to rank matches. This relevancy value is returned by the current search engine.

As noted above, there are several different standardized medical code sets. Data sets may be generated and/or accessed that identify relationships between code sets. The recommendation system may look for relationships in clinical data by 'cross-walking' a code. For example, a code for a new test or other service may be determined to be similar to an existing code for a similar test or service, or similar to multiple existing codes, or a portion of an existing code. By way of illustration, the process may cross-walk medication therapy management (MTM) services to SNOMED CT codes. By way of further example, the ICD-9 code 789.00 (Abdominal Pain, Unspecified Site) may be cross-walked to the IC-10 codes: R10.0 (Acute Abdomen) and R10.9 (Unspecified Abdominal Pain). For example, codes from different code sets within a physician's EMR that have been identified as being directed to the same subject matter (e.g., via a cross-walk table) may be treated as the same code by the system for purposed of generating a physician practice profile or for generating a patient's clinical profile. Thus, these code databases are used to improve the relevance scores of code matches to courses. The above results in a database of codes mapped to courses. The unique courses-mapped-to-codes database may be referred to herein as a 'SmartCME' database or data store.

The curated list of courses, generated by a recommendation algorithm, may be a dynamic list that may be changed in response to the recommendation system determining changes in the physician's EMR. For example, the system may update the list of recommended courses as patient codes are added to the EMR and as time elapses (and hence certain code entries have increasingly aged and may be assigned lower weight as compared to more recently entered codes), and as CME courses are added to and removed from the universe of CME courses. The recommendation process may perform some or all of the following states in generating recommendations:

build a weighted term vector for a given course, with common words (stop words) removed for natural language processing (although optionally removing stop words may be retained to facilitate phrase search). Certain sections of the course that are more likely to be indicative of the course content, may be weighted more heavily that other portions. For example, a course title may be more heavily weighted than a course description;

generate a query vector for a given code optionally using "OR" operations on code description terms (and optionally excluding stop words). Optionally, different terms may be differently weighted;

rank a code's query vector (where a query vector may include descriptive text and tags, code frequency, code volume, code entry dates, and the like) against a course term vector (where a course vector may include course descriptive text and tags) to determine a score. This results in a set of code scores for each course which may be stored in a data store. Optionally, only the more useful scores are stored for later access, such as those with relatively higher scores (e.g., those with the top 10 (or other threshold)) and/or those for the more common codes (e.g., those the 10 (or other threshold) most common codes), to reduce memory requirements and to speed up later mapping processes.

compute course relevance, at least in part, by multiplying each code score for the course by the volume of that code in the physician's practice profile. The practice profile may be reflected in the sum of codes in a practice group by code (the count of times each code was used). For example, the course relevance may be calculated using the following formula:

$$CR = \Sum_{(i=0)}^{n} [s\_i * v\_i]$$

CR=course relevance
s_i=course score for code i
v_i=practice volume for code i

Optionally, courses from one or more course providers may be recommended if they satisfy certain criteria. For example, filters may first be applied to available courses to generate a subset of courses. Optionally, the filters may include some or all of the following: location for live courses, preferred presenter(s), preferred course provider(s), preferred course type(s) (e.g., a video course, a text (article), a webinar course, live courses, downloaded courses, streamed courses, courses accessed via an application (e.g., a dedicated phone app, desktop app, etc.), etc.), preferred course length, preferred amount of learning credits, preferred maximum course price, preferred minimum course price, etc. The filtered courses may be further down selected by identifying those filtered courses having a score above a determined relevance score threshold to better ensure only courses with a high likelihood of relevancy to the physician are recommended.

An example patient program/course recommendation process will now be described. Certain aspects are similar to that for the physician recommendation process, while other aspects are specific to generating patient program/course recommendations. Patient programs can also include clinical trials or disease management programs, wherein opportunities for enrollment of the patient into a clinical trial or a disease management program may be presented to the patient.

Many patient clinical encounters are captured by a code in a physician's EMR, where a physician (inclusive of staff) will enter relevant codes for the patient into the EMR. The following is an illustrative example of how the clinical codes are utilized in a medical practice.

When a patient comes to a physician's office with a fever and rash, there is an initial diagnosis from the encounter that is captured using an ICD10 (International Classification of Disease) code. To confirm the diagnosis, the patient may be asked to have blood drawn, and a lab test may be run on the blood specimen, which may be captured using a LOINC code. To confirm the diagnosis, the physician may order an abscess be removed and pathology completed on tissue around the rash, and such process may be captured using a CPT (Current Procedural Terminology) code. To relieve the pain and rash, the physician may order a drug, which may be captured in an NDC (National Drug Code) code.

Many patient education programs may be related to at least one of these codes, and often, many of these codes. As an example, a patient program about Lyme disease may be linked to the codes for diagnosis, lab testing and drug therapy for Lyme disease. However, conventionally, an adequate map does not exist between the codes and the patient education programs. With such a map, the courses would be more valuable to the physician, patient, and publisher, as such a map enables relevant courses to be identified and recommended. As described herein, the recommendation system may be configured to generate such a map of codes to patient education programs.

Once a patient program is tagged with clinical codes, the program can be matched with a patient through the physician's EMR patient data set. For example, if a patient has Lyme Disease, then the diagnosis/lab/drug codes associated with Lyme Disease will be a part of that patient's record in the EMR dataset. Educational programs about Lyme Disease targeted for that patient can then be presented to the patient by their physician.

The process of building a targeted list of educational programs for a patient may be performed using some or all of the following process states:

the system tags patient educational programs with codes. For example, the system may perform a free text keyword search of patient-related program content (e.g., program title, abstract, summary, tags, content of the course itself, etc.) and of code-related information, perform comparisons, and identify matches. If course patient-related program content is identified that matches code-related information, an association between the corresponding program and code may be stored to provide a course-to-code mapping. By way of illustrative example, a program abstract or other related program text may be accessed and, in addition, code descriptions may be accessed that describes the code and its clinical context. The process may attempt to find keyword matches between the program abstract or other related course text, and the code descriptions;

optionally, as similarly described above, machine learning is utilized to aid in the generation of patient program recommendations. The map between codes and programs may dynamically evolve. Machine learning may be used to iterate through additional relationships among the programs and codes, to improve the process of how the recommendation system establishes the nexus/relevance between the codes and programs;

datasets may be utilized that have identified relationships between different code sets. Relationships in clinical data may be identified by 'cross-walking' a code. These additional databases of codes are optionally used to further describe the various types of code relationships to enhance the relevance scores of code matches to programs.

The foregoing process results in a database of codes mapped to patient education programs. The unique program-to-codes database may sometimes be referred to herein as 'SmartPatientEd' database.

The system may examine the patient dataset for a given patient as it exists in the patient's EMR. The system compiles a patient profile based on the patient (e.g., age, gender, residential address, profession, income, etc.). In addition, the system may parse the codes for the patient and determines i) volume of codes; ii) frequency of a unique code; and/or iii) date when the codes were added to the dataset.

These codes are captured to describe the patient profile. The volume, frequency, and/or date variables may be used in a formula to generate a relevance value from a combination of the weighted values of each variable. A list of codes may be built that describes not only the patient but also, optionally, the more recent trends in which codes are added to the EMR as a way to identify current patient encounters that indicate the patient's contemporary health profile.

Optionally, the recommendation system is architected to be agnostic as to which EMR vendor chooses to offer the physician and/or patient access to the curated list of patient education courses. APIs are optionally provided that enable the system software to access and input EMR data and patient profile data and generate and return a curated list of recommended courses to the EMR vendor for presentation to physicians within the vendor's EMR user interfaces (UI)/user experiences (UX) and/or to patients.

The system may run the 'SmartPatientEd' database against the top codes (e.g., the top 10 codes or other threshold of codes) from the patient profile to build a list of courses. As the system evaluates the list of matches, the system scores each match and generates a relevance score. The process may then rank the list of programs based on corresponding relevance scores.

"Relevance" may also informed by a user's preference information. A user interface is provided to allow end-user the opportunity to refine the type of patient education programs by indicating preferences. For example, a physician could set a preference for patient programs that focus on a specific procedure code or drug code as a way to address a specific patient population; they could indicate they prefer programs be associated with their hospital, located in San Francisco, Calif., etc.

Physicians can aid in the increase in program recommendation accuracy by adding preferences. By way of illustrative example, a user interface may be provided that enables physician to indicate a preference for patient education programs that focus on a specific procedure code or drug code as a way to address a specific patient population. The user interface may further enable the user to specify a preference for patient programs associated with a hospital where the physician has privileges. The user interface may also enable the user to specify a preferred location for live courses. For example, the user interface may indicate a preference for live courses located in San Francisco, Calif. The user interface may further enable the user to specify a preferred presenter, a preferred course provider, a preference for one or more course types (e.g., a video course, a text (article), a webinar course, live courses, downloaded courses, streamed courses, courses accessed via a dedicated or non-dedicated phone application, a computer application, etc.), a preference for a course length (e.g., 30 minutes, 1 hour, etc.), a preferred maximum course price, a preferred minimum course price, etc.

By filtering course recommendations based on preferences and the codes associated with the patient programs, the search process for patient programs to recommend is reduced, and the needed processing power is likewise reduced. Further, the speed associated with identifying programs to recommend is increased. Still further, the recommendation system may eliminate patient programs from consideration if those courses fall below a determined search relevance value (or threshold) generated by the system generates. The process for generating relevance values for patient programs selection is discussed in greater detail elsewhere herein.

Thus, as similarly described elsewhere herein, the recommendation system may perform some or all of the following:
map clinical codes to patient education programs for a patient;
create a new or enhanced patient education program record (a 'smart' program record) as the result of the patient education program being defined by relevant clinical codes;
build a patient profile (e.g., by evaluating the top or higher ranked codes in the patient's EMR by volume, code frequency, based on when codes were entered into the patient's EMR, code trending data).

As discussed elsewhere herein, a relevancy value may be generated from the evaluation that is specific to that program-code relationship, and the relevancy value may be used to rank matches.

The system may further improve determining the nexus between codes and programs by analyzing how codes are related to each other. As noted above, tables that 'cross-walk' an NDC to a ICD10 code to identify relationships between these codes may be utilized to further refine the nexus and may be used to inform the matching process and results. For example, codes from different code sets within a patient's EMR record that have been identified as being directed to the same subject matter (e.g., via a cross-walk table) may be treated as the same code by the system for purposed of generating a patient's clinical profile.

The curated list of patient programs, generated by a recommendation algorithm, may be a dynamic list that may be changed in response to the system determining changes in the patient's EMR. For example, the system may update the list of recommended programs as patient codes are added to the EMR and as time elapses (and hence certain code entries have increasingly aged and may be assigned lower weight as compared to more recently entered codes), and as patient programs are added to and removed from the universe of patient programs.

A given patient program may be provided to a patient via one or more channels using one or more media types. For example, a program may be provided to a patient terminal (e.g., a laptop, desktop, mobile phone, tablet, etc.) over the Internet as a downloaded file, via streaming, via email, via a short messaging service message, as a printed documents, or otherwise. The system can track a patient's access of and/or consumption of program and report such access and/or consumption to the patient's physician (e.g., via a reporting mechanism discussed herein).

Optionally, the physician may be provided with a list of the physician's recommend courses using a different interface than that used to present programs recommended for the physician's patients. For example, the physician may view courses (e.g., CME courses) recommended for the physician by accessing a corresponding control, such as a "CME Update" tab or section of the physician's EMR portal. The recommended patient programs for a given patient may be displayed to the physician when accessing the patient's unique record (EMR). The user interface presenting the recommended patient programs may enable the physician to select one or more of the programs (e.g., via respective links, checkboxes, or otherwise). The selection may be stored in memory and may be communicated to the patient (e.g., via an electronic communication, such as an email, short messaging service, application, web portal, or the like; and/or via directly by the physician when meeting with the patient).

A process for enrolling a physician in a course will now be described.

As similarly discussed above, the list of recommended CME courses may optionally be made available to the physician by the physician's EMR system via a course listing interface in response to a user activating a corresponding control, or automatically. The presented course listing may include (or may include a link to) a course title, presenter, user reviews, other course-related information discussed herein, and/or a course preview, in the form of a textual and/or video synopsis/abstract of the course, without leaving the EMR interface. A link may be provided, which, when activated, causes the access and presentation of additional detail on the course (e.g., credits offered, cost, available dates/times, etc.). The additional detail may be presented within the EMR system environment or outside of the EMR system environment (e.g., by accessing, using a browser, a URL associated with the course provider website).

A given course listing or course detail user interface may be presented in association with a course enrolment control. Activation of the control may cause an enrollment interface to be presented via which the user can register for and optionally pay for the course. The enrollment interface may be provided by the EMR system or may be hosted by, and provided by the course provider's online site. For example, a given course enrollment control may be associated with a URL to the enrollment user interface (e.g., hosted by the course provider's system), where activation of the enrollment control may navigate the physician's terminal to the corresponding enrollment user interface.

The recommendation system may transmit certain data elements to the course provider system (e.g., via an API) to assist in completing the physician enrollment form, and to validate that the recommendation system navigated the physician to the course provider site. Once the physician enrollment is completed by the provider system, and the enrollment information stored (e.g., the name of the physician, the course the physician enrolled in, the course date/time, payment information, etc.), the provider system may transmit an enrollment confirmation to the EMR system, optionally with a calendar message (e.g., including course name, date, time, location, etc.). The EMR system may add a calendar entry to the physician's calendar (which may be accessible via the EHR portal, or which may be a third party calendar application), which also may be used to cause alerts to be generated and provided to the physician (e.g., via pop-up notifications, audible notifications, short messaging service messages, or otherwise).

The provider system may optionally determine and track when the physician has completed a course (e.g., based on the physician electronically signing into a course, streaming a course, physically signing into a course, completing a course test or questioner, or otherwise). Once the provider system determines the course has been completed, the provider system may pass, over a network, a token to the EMR system, indicating that a certificate is available to certify that the physician has completed the course. Optionally, the provider system may automatically transmit the certification (e.g., in the form of an electronic document and/or code) to the recommendation system, which may store the certificate in a certificate library associated with the physician's account. This certificate can be retrieved from the certificate library by an authorized user of the physician's account and may be automatically or manually transmitted to a physician professional certification authority (e.g., a state medical board) system.

For example, the recommendation system may enable an authorized user of the physician account retrieve, via an interface, the competed certificate (e.g., in a report form that can be sent electronically or printed out). Scheduled reports can be electronically or via physical mail sent to multiple parties and destinations (e.g., designated by the physician and/or the recommendation system operator).

With respect to patient programs, as noted above, the recommendation system may track and record an indication that a patient has completed a recommended program. Optionally, the system may deliver a program completion indication electronically and/or physically to one or more designated destinations. Such completion designation may be presented to the patient's physician via an EMR user interface (e.g., in conjunction with patient's EMR system record).

Thus, a dynamic repository of continuing education courses and patient education programs that are defined by the clinical codes (the common vernacular of clinical medicine), is described. This classification system enables physicians to streamline access to their CME and MOC material and to meet their certification needs.

Aspects of the disclosure will be discussed with respect to the figures.

Figure 1B:
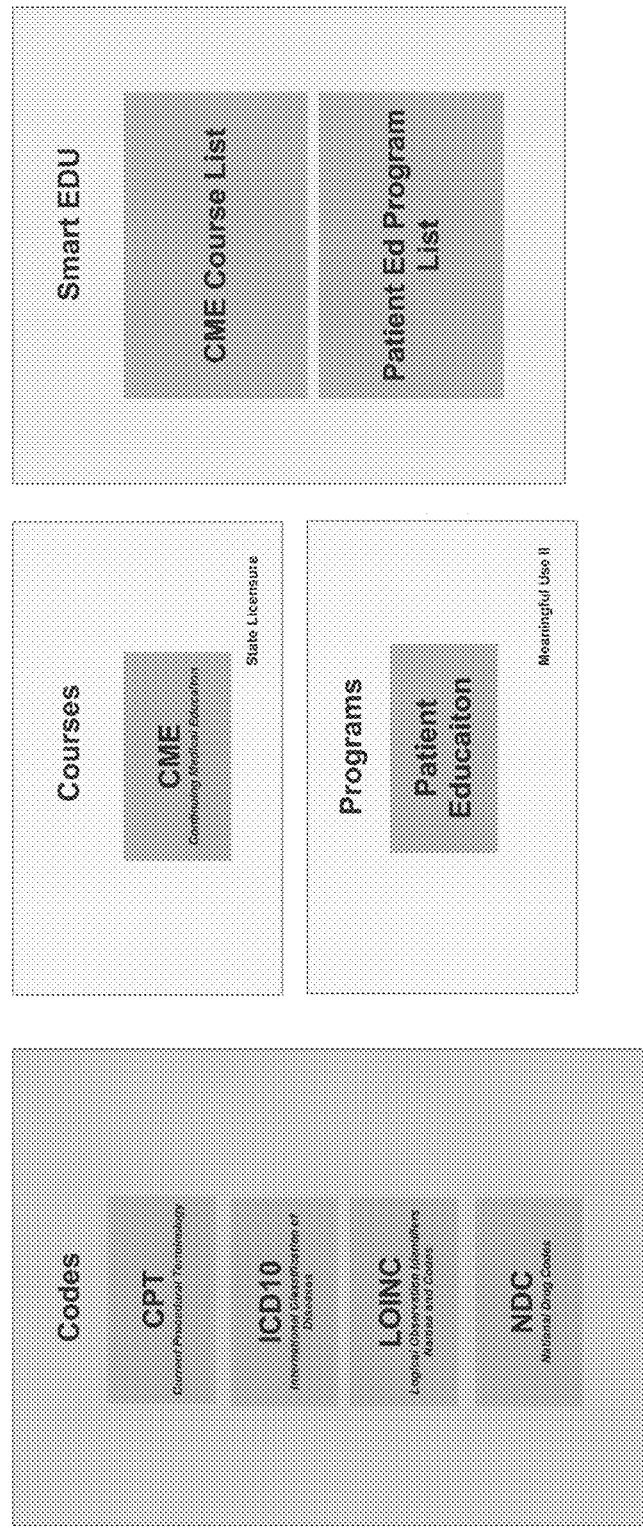
FIG. 1B illustrates an example data flow.

FIG. 1B illustrates an example data store architecture. A code data store may store one or more types of codes, such as clinical codes (e.g., ICD10, MESH, CPT, NDC, HCPCS, LOINC, SNOWMED, etc.), and associated code descriptions. The codes may have been accessed over a network from one or more code authority databases. The codes may be associated with respective textual tags or other descriptive information. A course data store may store data that describes educational courses (e.g., for physicians). The course data store may include, for a given course, a course name/title, a course abstract, other course descriptive information (e.g., tags), and/or other course data. The course data may have been accessed from one or more course providers. A program data store may store data that describes educational programs or clinical trials (e.g., for patients). The program data store may include, for a given program, a program name/title, a program abstract, and/or other program data. The program data may have been accessed from one or more program providers. A smart EDU data store stores an association of courses with relevant codes, and an association of programs with relevant codes, where the code relevancy is determined as described elsewhere herein.

Figure 2:
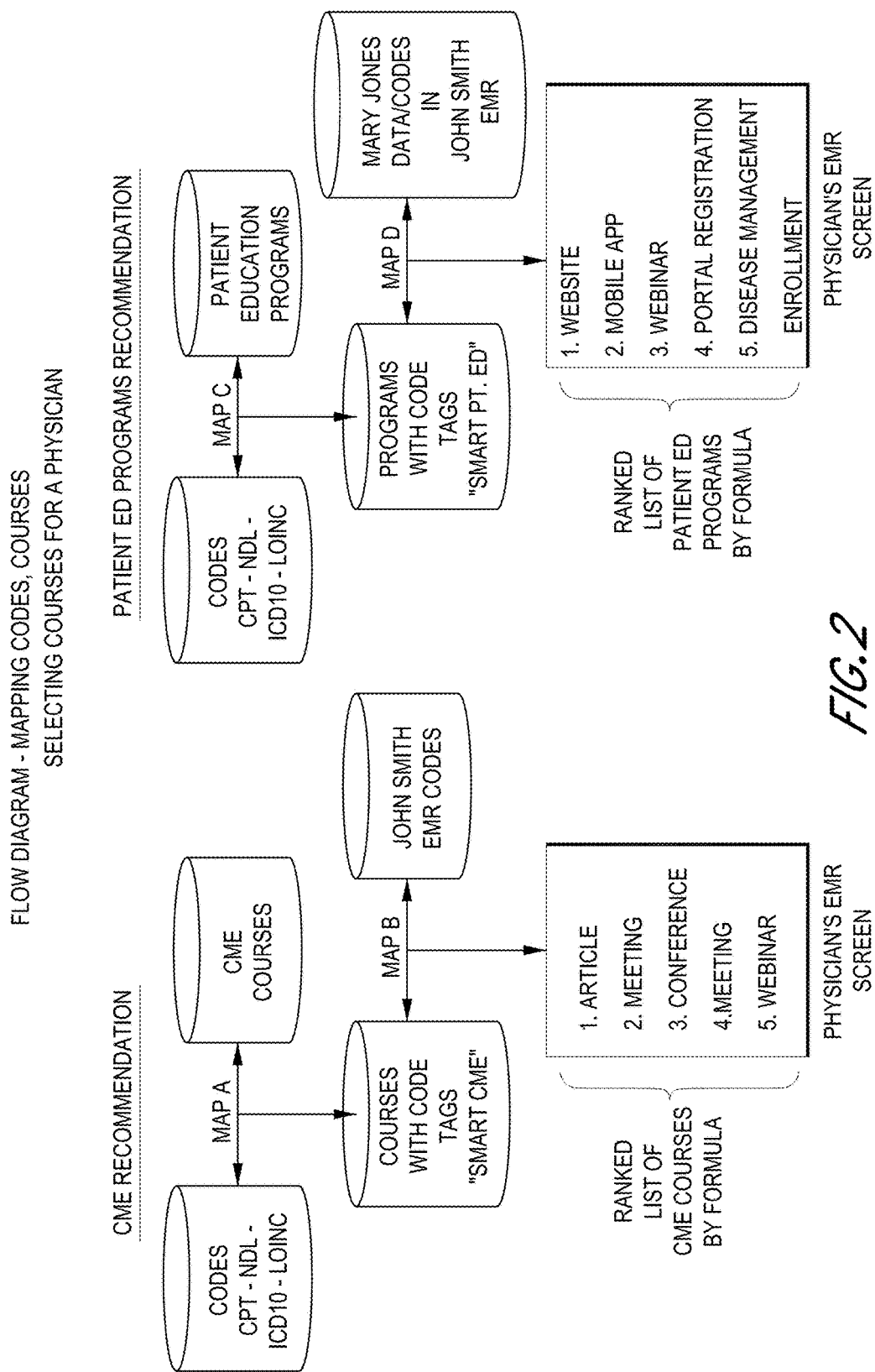

FIG. 2 illustrates example processes for generating course recommendations for a medical professional (e.g., a physician) and for generating a patient recommendation for a patient. The process may be performing using the example recommendation system described herein.

With respect to generating course recommendations for a medical professional, one or more sets of codes are mapped to courses (e.g., CME courses) from one or more course providers to generate a data store that maps courses with code tags (referred to in the following example as Map A). The mapping may be performed using the corresponding data stores illustrated in FIG. 1B. The mapping may be generated by comparing words used to describe the codes and the words used to describe the courses. A relevance score is created from this mapping and the codes are ranked and listed based on their relevance score from highest relevance score to lowest relevance score for each course. The medical professional's EMR patient codes are analyzed and the analysis result is compared to the mapped courses as described elsewhere herein. Relevance scores are created from this mapping (referred to in the following example as Map B). A ranked list of recommended courses is generated using the relevancy scores, as described elsewhere herein, and the ranked list of recommended courses (which may include course name, course format (e.g., website, webinar, mobile app, article, meeting, conference, etc.), a brief course description, and/or a link to course information) is provided to the medical professional (e.g., using an EMR user interface) via a physician's terminal. Optionally, the list of recommended courses is generated using physician specified preferences as described elsewhere herein.

With respect to generating program recommendations for a patient, one or more sets of codes are mapped to programs (e.g., patient programs) from one or more program providers to generate a data store that maps programs with code tags (referred to in the following example as Map C). The mapping may be performed using the corresponding data stores illustrated in FIG. 1B. The mapping may be generated by comparing words used to describe the codes and the words used to describe the programs. A relevance score is created from this mapping and the codes are ranked and listed based on their relevance score from highest relevance score to lowest relevance score for each program. The patient's EMR codes are analyzed and the analysis result is compared to the mapped programs as described elsewhere herein. Relevance scores are created from this mapping (referred to in the following example as Map D). A ranked list of recommended programs (which may include course name, course format (e.g., website, webinar, mobile app, article, meeting, conference, etc.), a brief course description, and/or a link to course information) is generated using the relevancy scores, as described elsewhere herein, and the ranked list of recommend programs is provided to the medical professional (e.g., via an EMR user interface) via a physician's terminal. The physician may optionally select one or more programs for referral to the patient. Optionally, the list of recommended programs is generated using physician and/or patient specified preferences as described elsewhere herein. Optionally, the ranked list of recommend programs is provided to a patient device (e.g., via a web page, a dedicated application, or otherwise).

Figure 3:
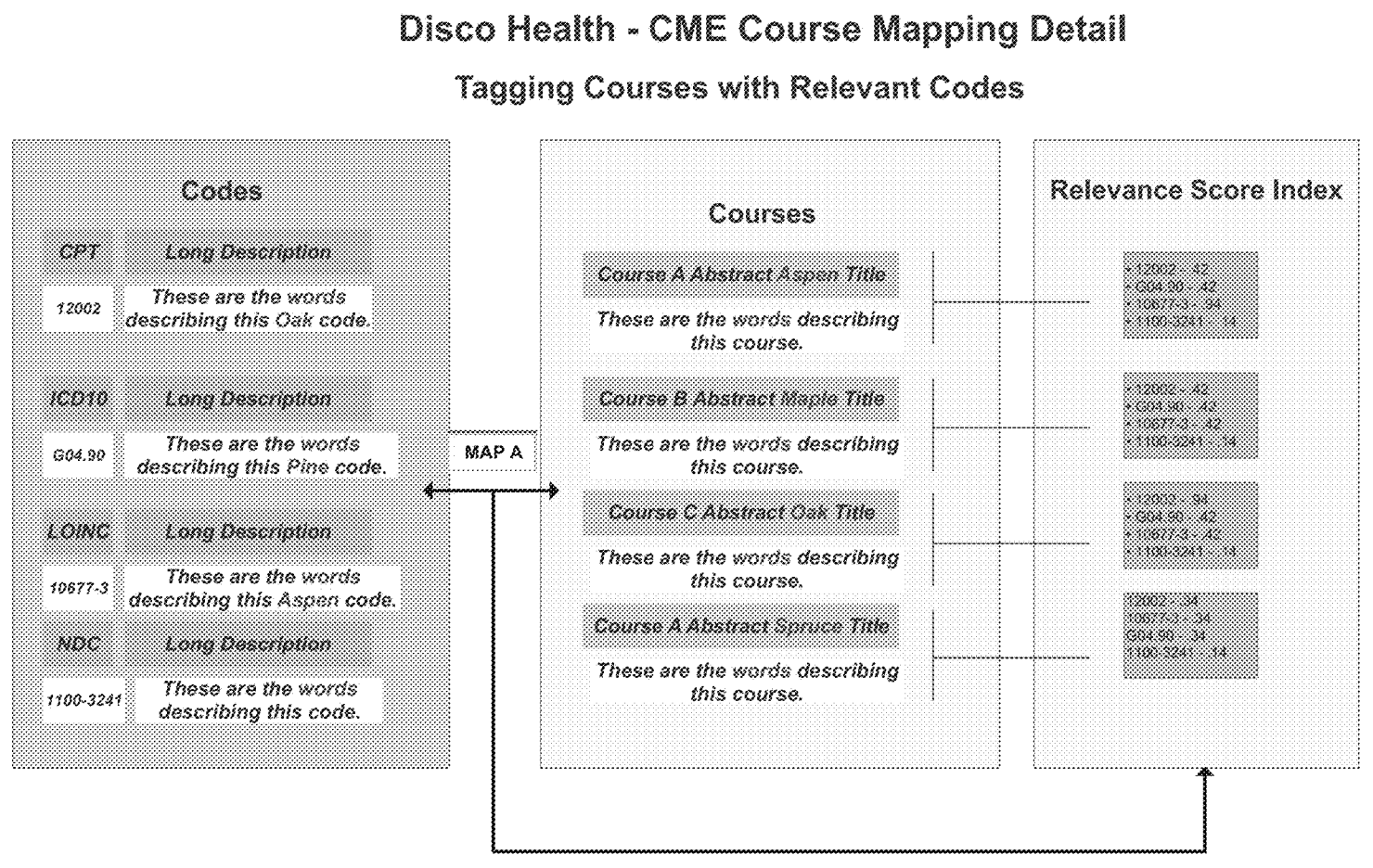

FIG. 3 illustrates an example code mapping process that maps codes and courses (e.g., CME courses) to generate a map, such as Map A referred to above. The code data store may include codes from multiple code standards (e.g., CPT codes, IC10 codes, LOINC codes, NDC codes, and/or other codes). A given code entry may identify the associated standard, the associated unique alphanumerical code, and provide a textual description. The course data store may store course data from multiple sources. A given course entry may include a unique course identifier code, a title, an abstract, and other textual description. A relevance score is generated for a given course as a result of the comparison of the code data with the course data, based at least in part on identified matches between keywords or phrases found in the code data and the course data. A code that has same keywords found in data for a course is given a higher relevance score than a code that does not have any of the same keywords found in data for the course. A relevance score index may be generated for each course indicating the scores for a given code. Optionally, to reduce memory, only codes with a score meeting a certain threshold level are stored.

Figure 4:
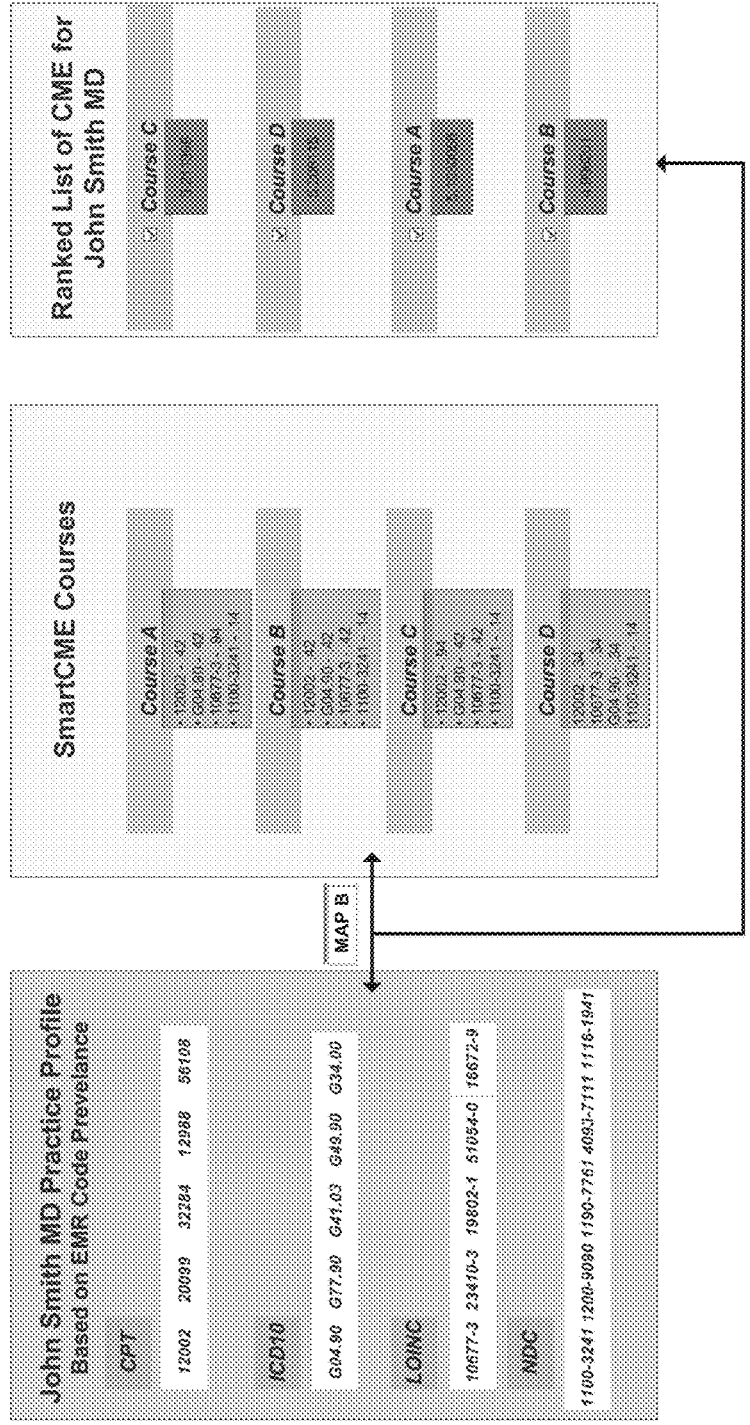

FIG. 4 illustrates an example process of mapping codes, that are specific to a physician's EMR, to CME courses that have been tagged with codes to generate a map, such as Map B referred to above. As similarly discussed elsewhere herein, the codes in the EMR may be examined and a determination made as to the volume of codes, the frequency of a given code, dates when the codes were added to the physician's EMR, and/or the trending of the frequency of when the code was entered into the EMR. Codes meeting a certain threshold (e.g., the top 5 codes in frequency over the last 12 months) in a given code category may be identified. The identified codes may be used to describe a profile of the physician's practice and the patterns in the physician's practice. By way of illustrative example, a code that occurs 1,200 times in the EMR of the physician's patients over the past 10 years may be considered as important (or more important) as a code that occurs 600 times in the past 4 years, or as important as a code that appears 300 times in the past 12 months. The relevance value of the code in the practice profile is optionally scored using a formula that considers all three of the foregoing factors or a subset thereof.

Once the top codes, meeting a certain threshold, are selected from the physician's practice profile, these codes are then mapped to the CME courses that have been tagged with codes (e.g., Map B). A relevance score may be generated based on the comparison of the two sets of data. In particular, the relevance score may be based, at least in part, on the frequency of the codes from the practice profile that match the codes tagged to the courses. By way of example, a course associated with multiple codes that match multiple codes in the practice profile may be given a higher relevance score than a course with no codes that match any codes in the practice profile.

Figure 5:
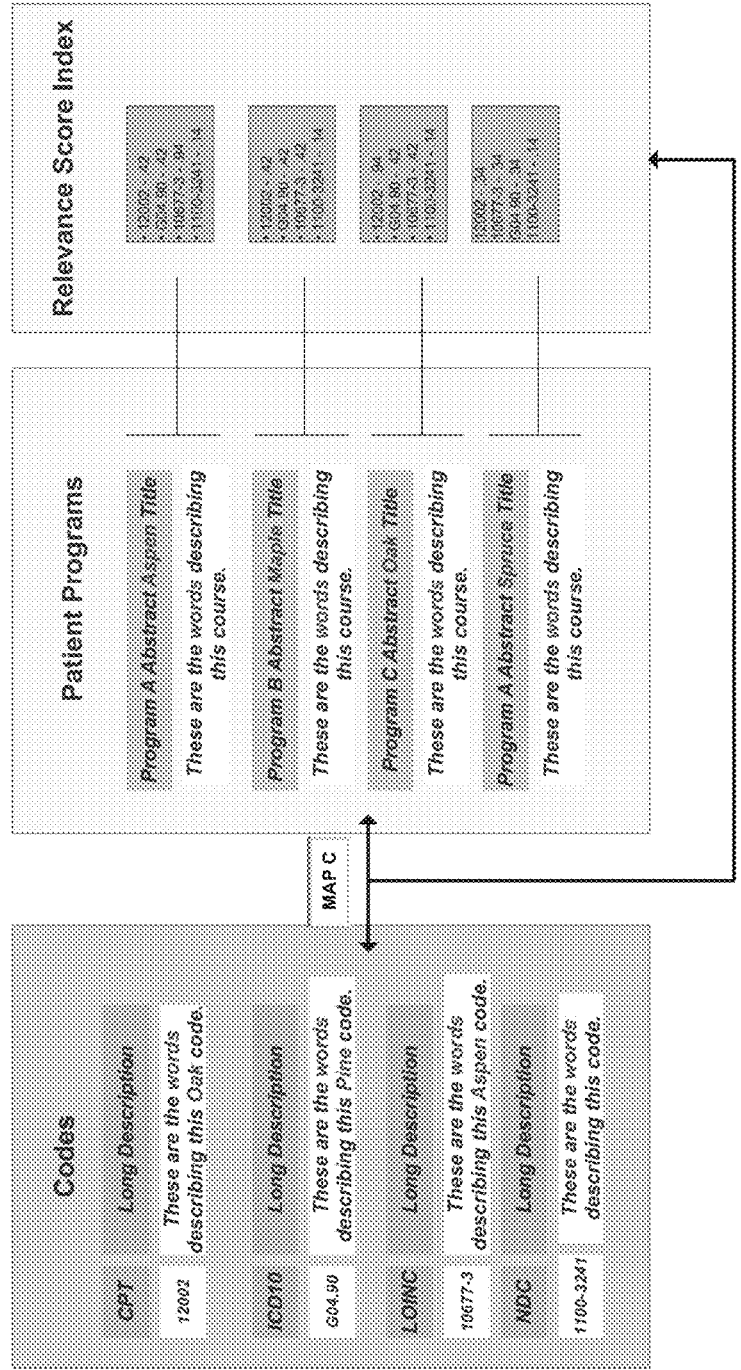

FIG. 5 illustrates an example code mapping process that maps codes and programs (e.g., patient courses or trials) to generate a map, such as Map C referred to above. The code data store may include codes from multiple code standards (e.g., CPT codes, IC10 codes, LOINC codes, NDC codes, and/or other codes). A given code entry may identify the associated standard, the associated unique alphanumerical code, and a textual description. The program data store may store program data from multiple sources. A given program entry may include a unique program identifier code, a title, an abstract, and other textual description. A relevance score is generated for a given program as a result of the comparison of the code data with the program data, based at least in part on identified matches between keywords or phrases found in the code data and the program data. By way of example, a code that has same keywords found in a program is given a higher relevance score than a code that does not have any of the same keywords found in a program. A relevance score index may be generated for each program indicating the scores for a given code. Optionally, to reduce memory, only codes with a score meeting a certain threshold level are stored.

Figure 6:
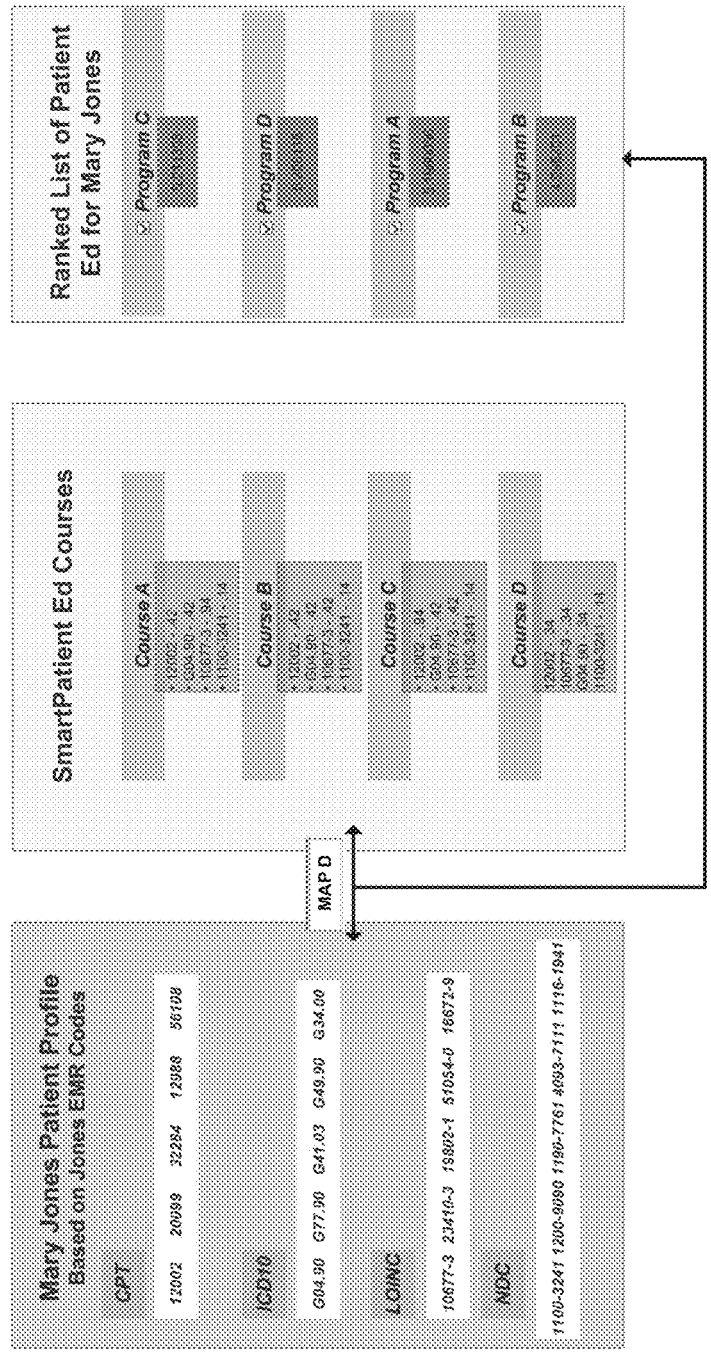

FIG. 6 illustrates an example process of mapping a patient's unique codes in the physician's EMR to patient programs that have been tagged with codes to generate a map, such as Map D referred to above. As similarly discussed elsewhere herein, the codes in the EMR records of the patient may be examined and a determination made as to the volume of codes, the frequency of a given code, dates when the codes were added to the physician's EMR, and/or the trending of the frequency of when the code was entered into the EMR. Codes meeting a certain threshold (e.g., the top 5 codes in frequency over the last 12 months) in a given code category may be identified. The identified codes may be used to describe a clinical profile of the patient's health and the patterns in the patient's health conditions. By way of illustrative example, a patient code that occurs 20 times in the patient's EMR records over the past 10 years may be considered as important as a code that occurs 10 times in the past 4 years, or as important as a code that appears 3 times in the past 12 months. The relevance value of the code in the patient profile is optionally scored using a formula that considers all three of the foregoing factors or a subset thereof.

Once the patient codes are selected from the patient's profile, these codes may then be mapped to patient programs that have been tagged with codes (e.g., Map D). A relevance score is generated based at least on the frequency of the codes from the patient profile that match the codes tagged to the programs. A program with multiple codes that do not match any codes in the patient profile is given a lower relevance score.

FIG. 1A illustrates an example architecture and example processes. The illustrated architecture and processes may be used to create or identify healthcare resources to advance knowledge of specific health and clinical medicine topics. An intermediary recommendation system (DISCO HEALTH in this example) analyzes and compares codes and courses/programs with the outcome of a targeted list of education material for a health service provider (e.g., a licensed medical doctor or medical professional who has the legal credential to deliver health care diagnosis and treatment related counsel) and their patients (e.g., a person consulting with the health provider to diagnose or treat or assess a health condition). The recommendation system builds a store of the clinical codes and related code descriptions (e.g., descriptions, unique code identifiers among other descriptive data). The codes may be accessed by the system from publically accessible databases and are stored in a clinical codes database.

An example recommendation system may include a web services API to access data from an EHR system. The data may be provided to a pattern practice engine and to a patient profile generation engine. The pattern practice engine may access CME course metadata (e.g., that stores course names, abstracts, other descriptive text, and/or other information described herein) stored in a course metadata database. The course metadata may have been retrieved over a network from a course provider system (e.g., a CME course provider that has a database of CME courses and related data). The pattern practice engine may generate a practice profile for the medical provider by aggregating clinical codes that reside in that physician's EMR (referred to herein as Patient Aggregated Data) through the API that calls for and organizes the clinical codes (e.g., based on a National Provider Identifier "NPI" number). As described elsewhere herein in greater detail, the profile may be generated from an evaluation and organization of the code volumes, the dates when the codes were logged into the EMR system and a trend line that looks at both volume and time.

Similarly, the patient profile generation engine may accesses patient program metadata (e.g., that stores program names, abstracts, other descriptive text, and/or other information described herein) stored in a program metadata database. The program metadata may have been retrieved over a network from a patient program provider system that has a database of CME course and related data. It is understood that a given system can provide information for both CME courses and patient programs.

The system may build and store a patient profile ("Mary Smith Bio" in the example) by aggregating the clinical codes stored in the physician's EMR system records for the patient accessed via the API, that calls for and organizes the clinical codes based on the patient identifier in the EMR. As discussed elsewhere herein in greater detail, the system may generate the patient profile based at least in part on an evaluation and organization of the code volumes, the dates when the codes were logged into the EMR and a trend line that looks at both volume and time. The system may also search for specific information about the patient such as the patient's problem list, medications list, and/or lab results.

A mapping engine performs the mapping operations such as the example mapping operations described elsewhere herein (mapping of courses to codes, mapping of a physician profile to courses, mapping of programs to codes, mapping of a patient profile to programs). Customized lists of recommend physician courses and patient programs may be generated and provided to an interface module residing on the physician's EHR system for display to the physician on a physician terminal, as discussed elsewhere herein. The recommended courses/programs may be ranked according to calculated relevancy scores. Optionally, only those courses/programs that satisfy a certain threshold (e.g., having a relevancy score above a certain threshold, or that are within a certain number of top ranked scores, such as within the top 10 ranked courses/programs) are presented in the recommendations.

Optionally, a user interface is provided via which the user can alter the sensitivity of the course relevance score to increase the number of courses presented by lowering the relevance score threshold or to decrease the number of courses presented by raising the relevance score threshold. Optionally a relevance threshold slider control is provided with pre-set relevance settings that instructs the system to adjust the relevance setting for the user with a simple movement of the slide to the left (see more courses) or right (see fewer courses). The system may use the slider setting in selecting the number of recommended courses to present.

An enrollment module enables the physician to enroll or register in the course by providing access to a program enrollment module and a login module hosted by the content provider system. A token may be passed between the intermediate recommendation system and the course/program provider system to enable the course/program provider system to identify the source of the inquiry and to allow the system to properly track the certification of course completions.

A tracking module receives, from the content provider system, information as to which courses the physician enrolled in and which courses the physician completed. The tracking module may receive, from the content provider system, information as to which courses the physician's patients enrolled in and which courses they completed. The recommendation system may use this information to track educational credits earned and to generate reports indicating the courses/programs completed and associated credits, which may be transmitted to determined destinations, such as the patient, the payer (e.g., an insurance company of the patient), a CMS system, a certification entity system (e.g., a state board of medicine system), or other such entities and associations. An example report is described elsewhere herein in greater detail. The system may be configured to analyze and share data collected from the mapping processes, and from user interactions with the system that indicate course/program selections, practice profiles, patient profiles, physician preferences, course/program completions, total number of credits earned, and/or other data discussed herein.

Security and encryption protections are optionally provided in the processing and storing of the data handled by the system (e.g., patient data, physician data, course provider data, program provider data, certification data, tracking data, etc.).

FIG. 7 illustrates an example physician user interface that enables a physician to access and interact with a recommended course list for the physician (e.g., a CME course), which may have been generated using the processes discussed above, such as the mapping and relevance determination processes. The user interface and/or the data provided therein may have been generated in whole or in part by the recommendation system. In this example the user interface is accessed via a CME tab that is appended to the physician's standard EMR interface. Optionally, the CME user interface may be accessed via other techniques such as a menu or otherwise. The user interface presents the generated list of recommended courses, optionally organized by type of CME activity that is available for registering. For a given listed CME the system provides, via the user interface, one or more of the following may be provided: i) summary view of the course information (e.g., provider name, course name, instructor/faculty, number of credits, a course abstract or link thereto; ii) a control that enables course enrollment or registration; iii) access to course certificate (upon course completion); iv) a view of the completed credits earned by the physician from completing the course; v) a report of the current state of their CME to selected authorized associations.

FIG. 8 illustrates an example user interface that enables a physician to access and interact with a recommended program list for a patient, which may have been generated using the processes discussed above, such as the mapping and relevance determination processes. The user interface may have been generated by the recommendation system. The user interface is optionally provided inside (at the same time as) the electronic patient record stored in the physician's EMR system, or in response to a control (e.g., presented in conjunction with the patient record) activated by the physician. Thus, the user interface of recommended patient programs may be made available to the physician and the patient during a patient encounter (a patient appointment with the physician). This view enables the physician to select a program for the patient and cause the program to be delivered to the patient. Optionally, a mode interface is provided via which the physician and/or patient to specify a delivery mode (electronic delivery, print delivery, download, streaming, text message, physical mail, etc.). Optionally, in response to determining that an electronic address is not provided or available, the system may automatically select a print mode (e.g., paper print out, DVD (e.g., for a video course), USB memory drive, etc.) to enable the program to be handed to or physically mailed to the patient.

FIG. 9 illustrates an example preference specification user interface via which a physician can enter and review preferences. The system, via information received via the user interface, enables the physician to influence which CME courses are selected for recommendation, beyond the mapping of the codes and courses. For example, the user interface enables the physician to specify course locations (e.g., specific venues for meetings), course authors or presenters, topics of interest, procedures of interest, and/or courses associated with specific codes. The specified preference may then me utilized in generating course recommendations as discussed elsewhere herein.

Figure 10:
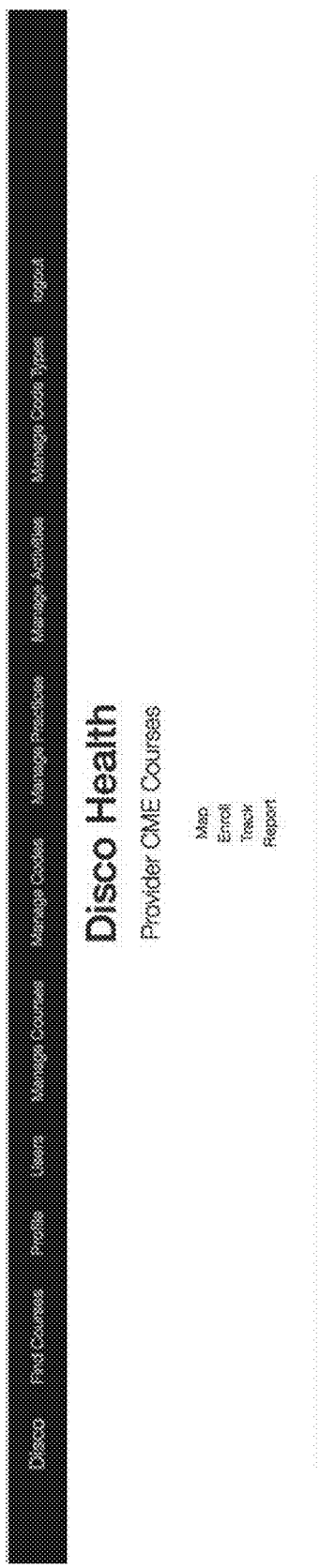
Figure 11:
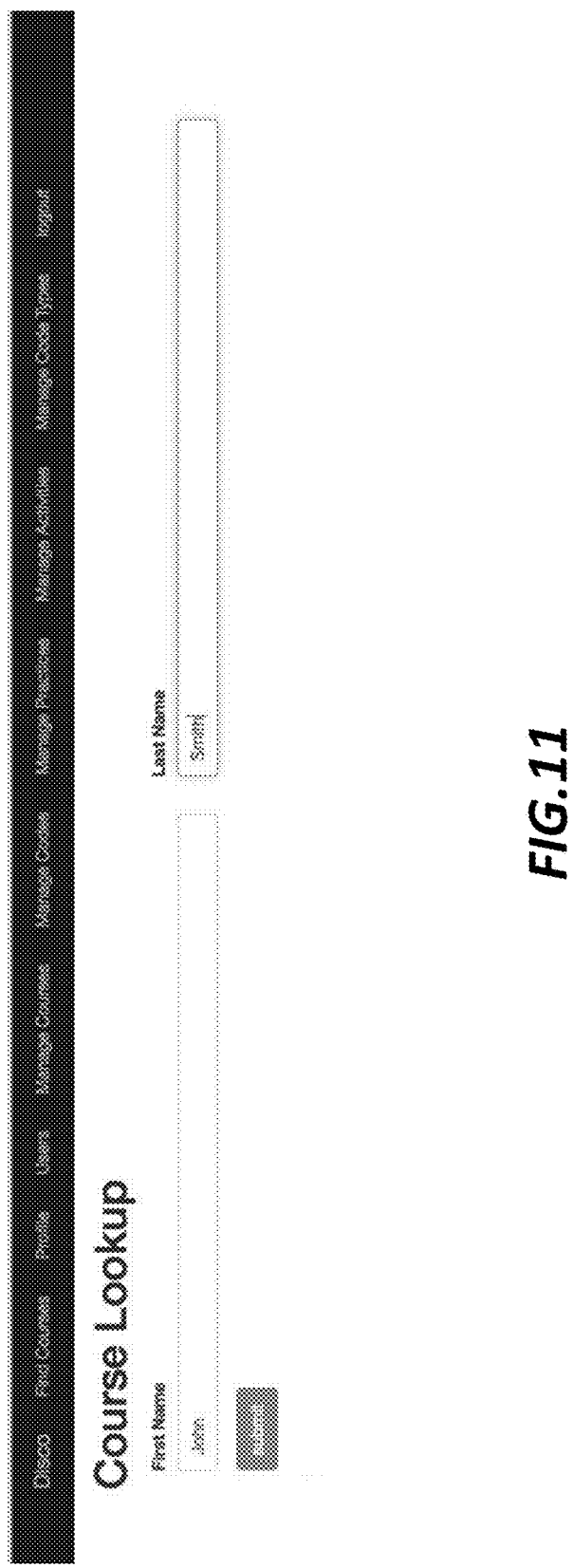

FIG. 10 illustrates an example user interface of a portal main page. The user interface includes links to a map user interface, an enroll user interface, a track user interface, and a report user interface. FIG. 11 illustrates an example user interface that enables an administrator to enter a name of a physician in the system portal in order to generate a list of curated recommended courses.

FIG. 12 illustrates an example list of generated CME course recommendations, sorted by the calculated relevance values. The listing provides the course title, cost, location, relevance values, and dates. Optionally, the user interface enables the user to sort the list by title, cost, location, relevance value, or dates. Date, location, and cost filters are provided via which the physician can further filter the recommended course list.

FIG. 13 illustrates an example course detail user interface for a recommend course. The user interface provides a practice type, an activity type, a location, number of credits, cost, description, provider, and an indication as to whether the course is commercially sponsored. "Practice Types" represents the various disciplines that a physician would practice that are relevant to the physician. This field helps to refine the courses selected by the system. "Activity types" represents the different type of educational courses that are available for the physician (e.g., live course, meeting, a webinar, text journal article, a video, audio only, streaming, download, etc.). "Credits" represents the numerical value of the credit that is awarded for completion of the course. For example, a physician may be required by their state and various other professional associations to complete a certain number of credits in a defined period of time to maintain licensure or good standing. "Commercially sponsored" represents the commercial organization, if any, that financially supported the course development.

Figure 14:
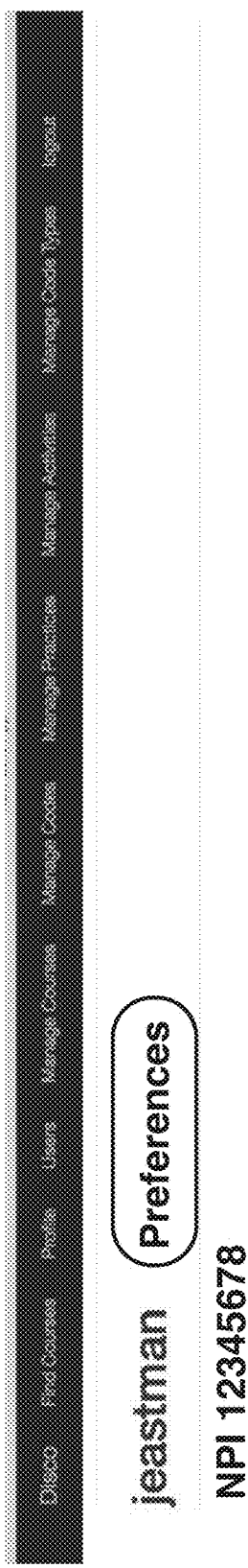

FIG. 14 illustrates an example physician's profile user interface, providing the physician's name or user identifier, NPI number, and a link to the physician's preferences.

Figure 15:
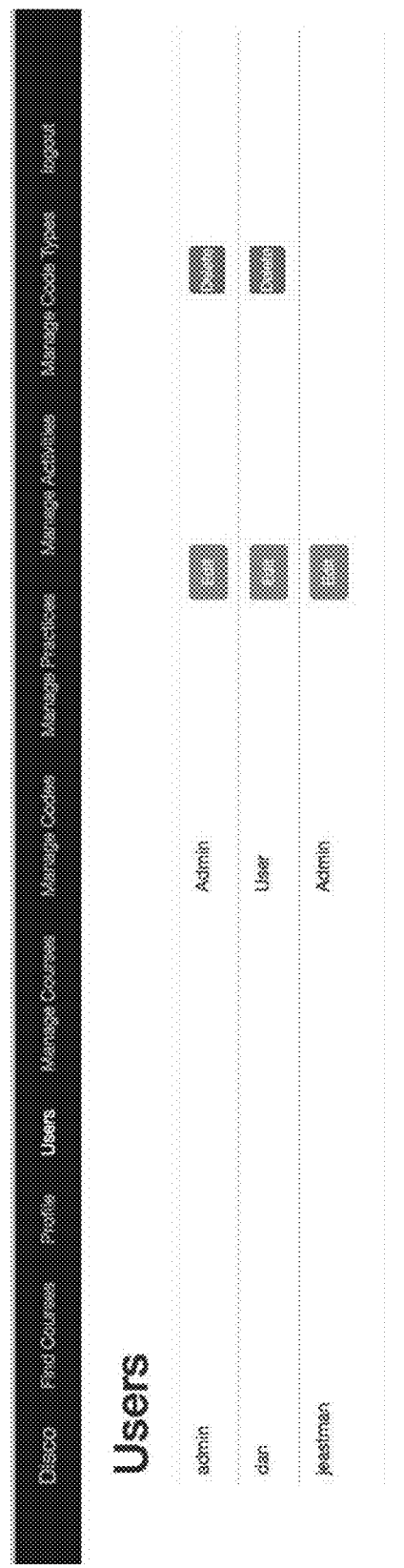

FIG. 15 illustrates an example administrator user interface that provides a list of users authorized to access the system and their role/level of authorization (e.g., admin, user, etc.). An edit control is provided that enables the administrator to edit the entries. A delete control is provided that enables the administrator to delete entries (so that the corresponding user may no longer access the system).

Figure 16:
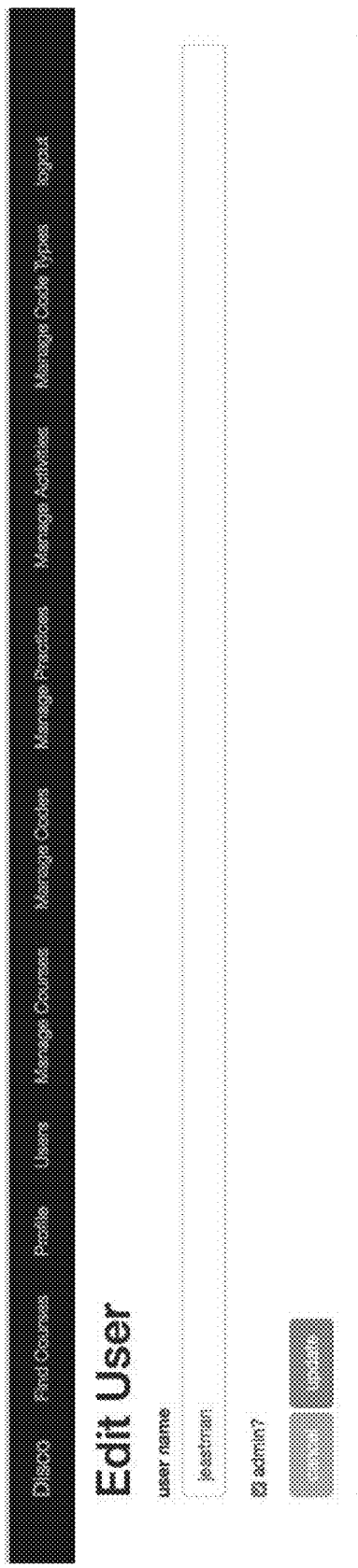

FIG. 16 illustrates an example user interface that enables an administrator to edit a record of a user authorized to access the system portal.

Figure 17:
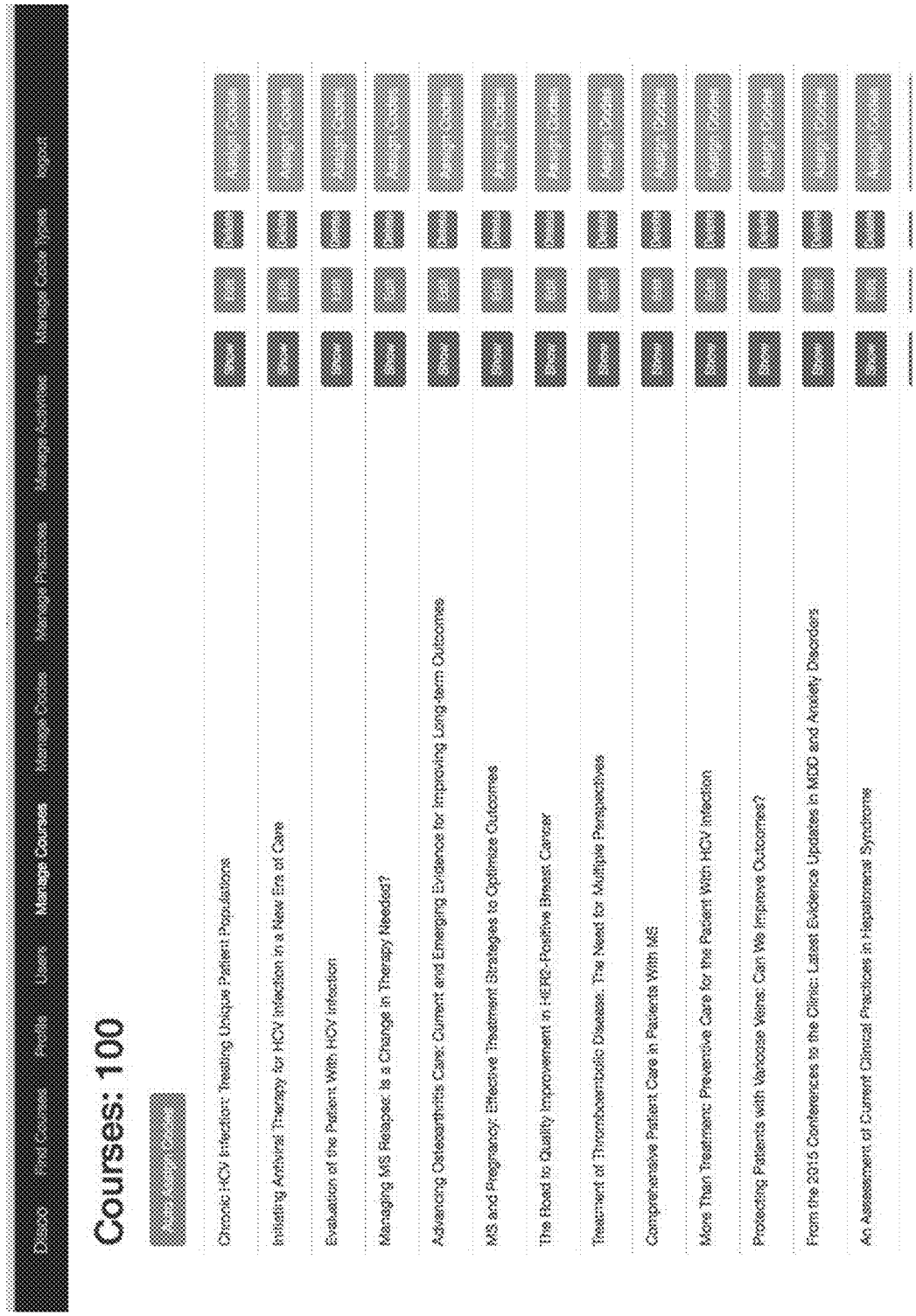

FIG. 17 illustrates an example administrator user interface providing a list of CME courses and patient education programs that are available via the system portal. Show, edit, delete, and assign controls are provided. Activation of the show control causes additional course information to be accessed and displayed. Activation of the edit control causes a course entry edit user interface to be displayed. Activation of the delete control causes the course to be deleted from the record of courses. Activation of the assign codes user control initiates a code assignment process.

FIG. 18 illustrates course details user interface, providing details and the data elements associated with a CME course (e.g., practice type, activity type, location, credits, cost, description, provider, an indication as to commercial sponsorship).

Figure 19:
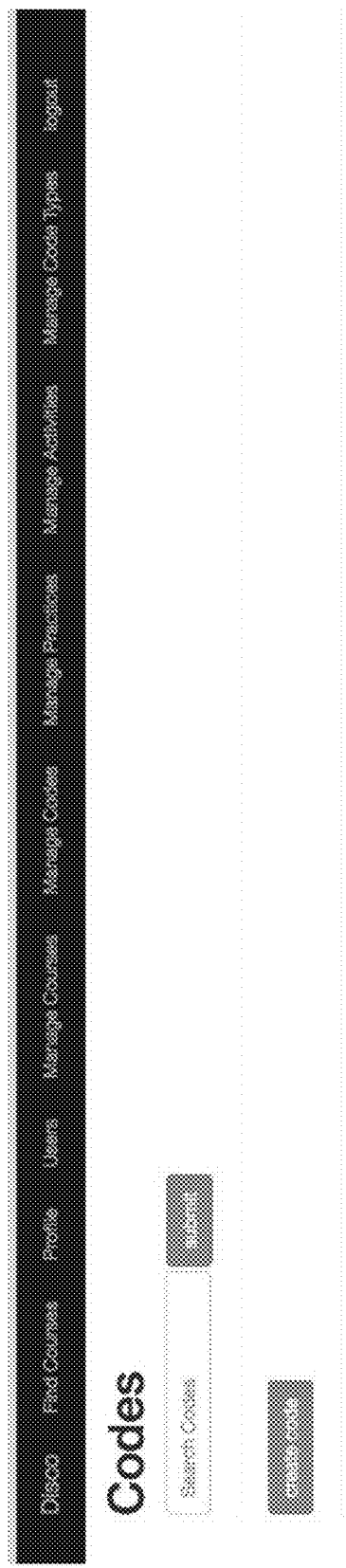

FIG. 19 illustrates a user interface that enables an administrator to search for codes. The user interface includes a search codes field, and a query submit control. In addition, a create code control is provided.

Figure 20:
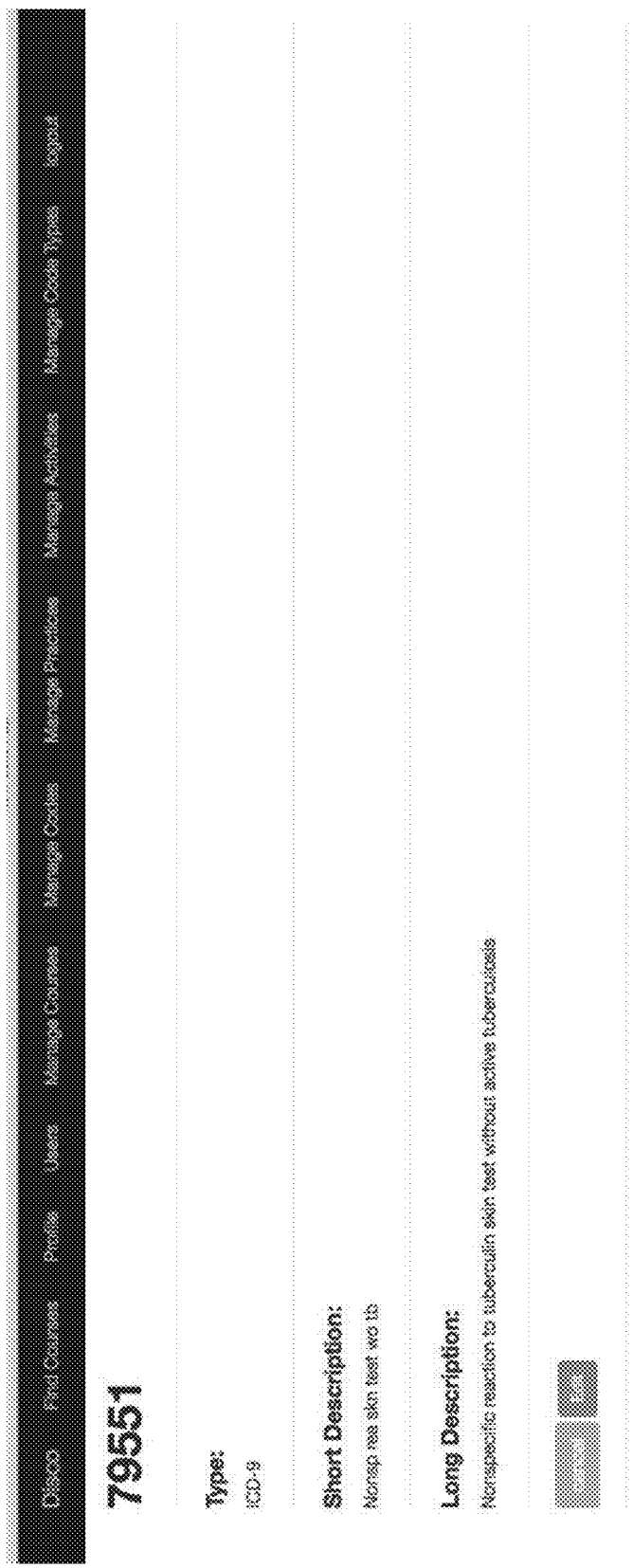

FIG. 20 illustrates an example user interface providing details on a code. For example, the user interface may be presented in response to a code search query entered using the user interface of FIG. 19. The user interface may present the code, the code type (the name of the code set, such as ICD-9), a short description of the code, and a long description of the code. An edit control enables an administrator to edit the code details.

Figure 21:
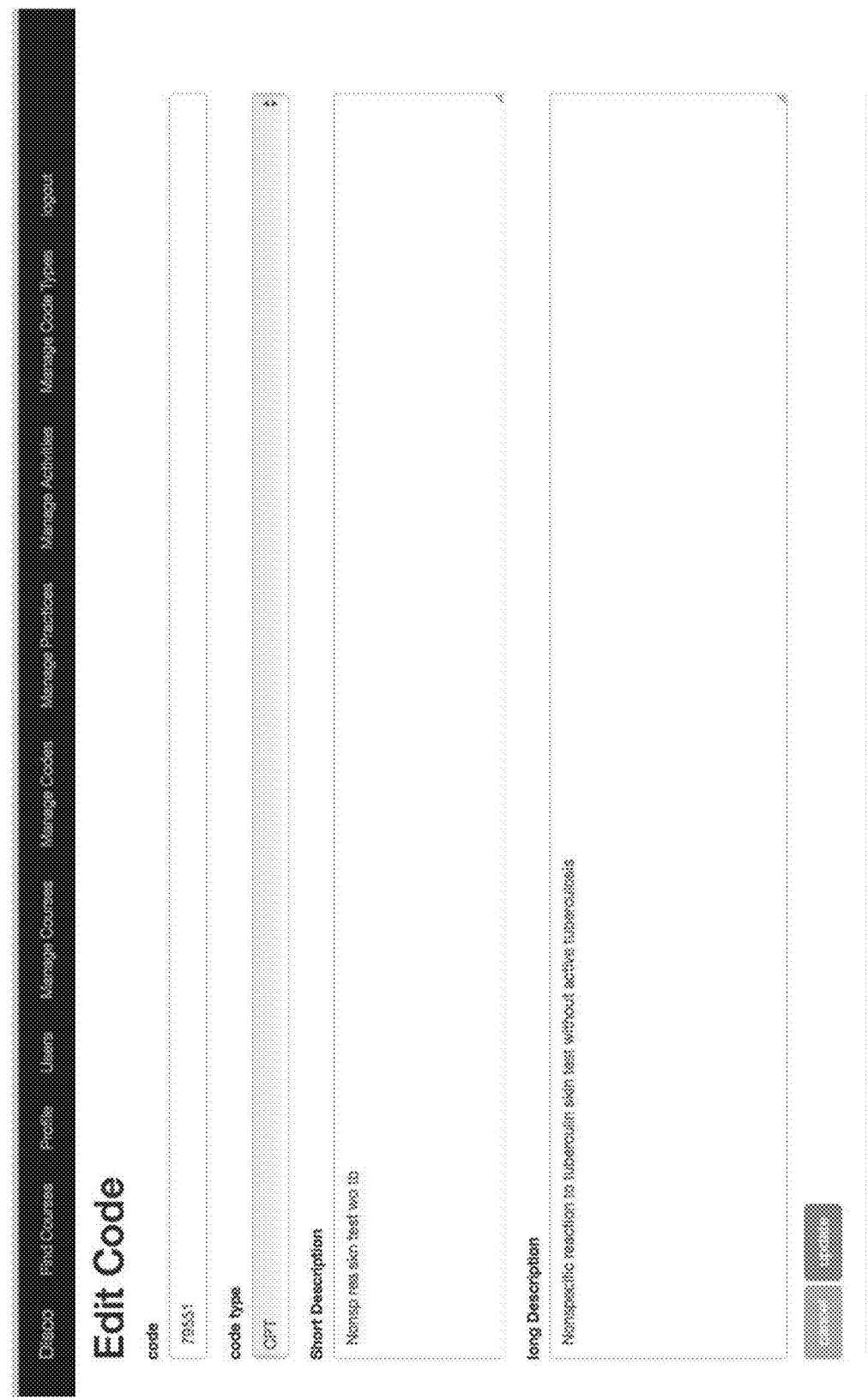

FIG. 21 illustrates an example code details user interface, which may be presented in response to activation of the edit control illustrated in FIG. 20. The user interface enables the code, the code type, the short description of the code, and the long description of the code to be edited. The edited details may then be used to update the corresponding code details record, which will be stored in memory.

Figure 23:
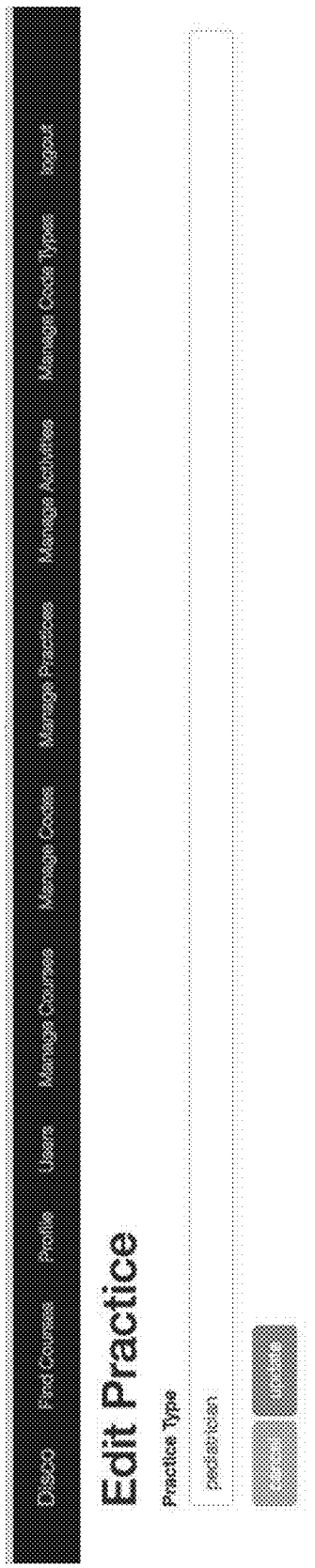
Figure 24:
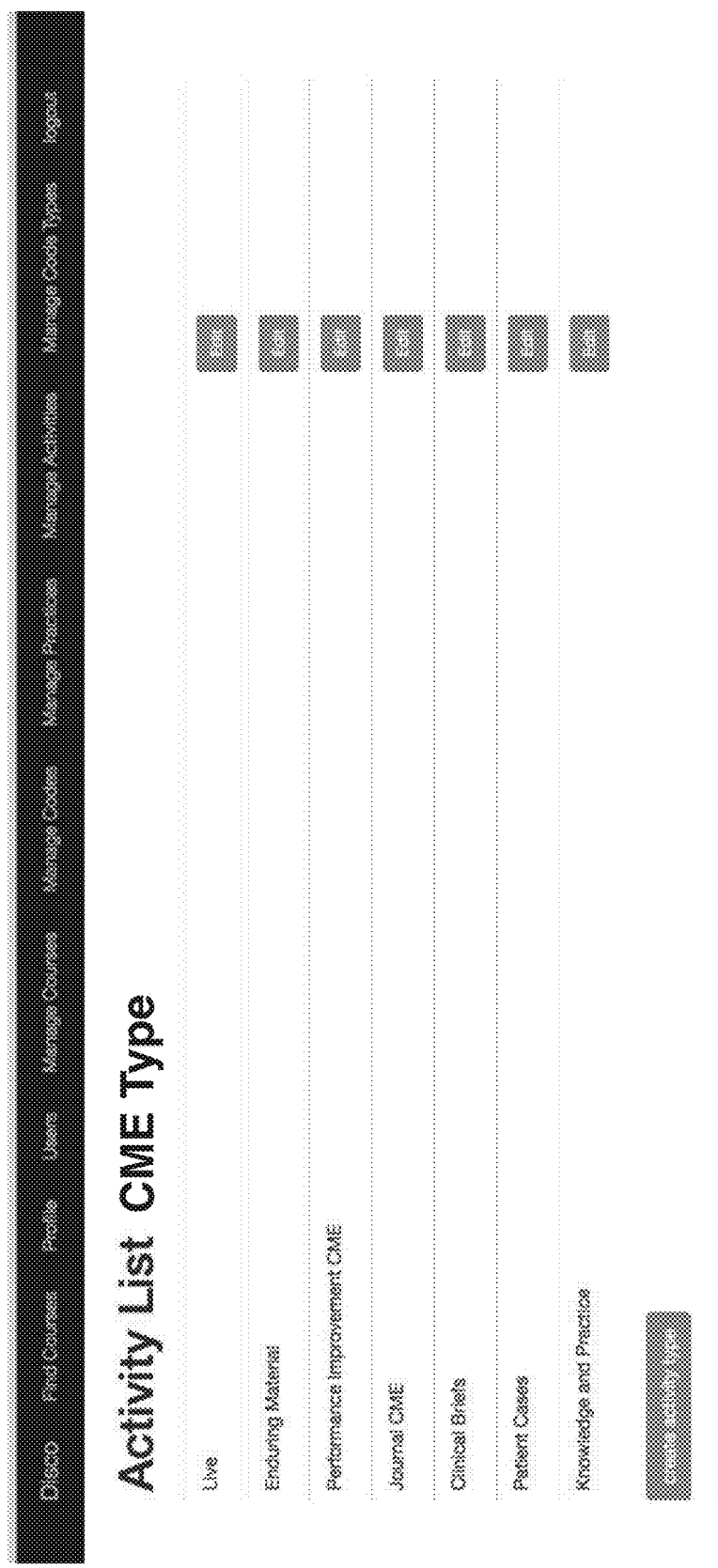
Figure 25:
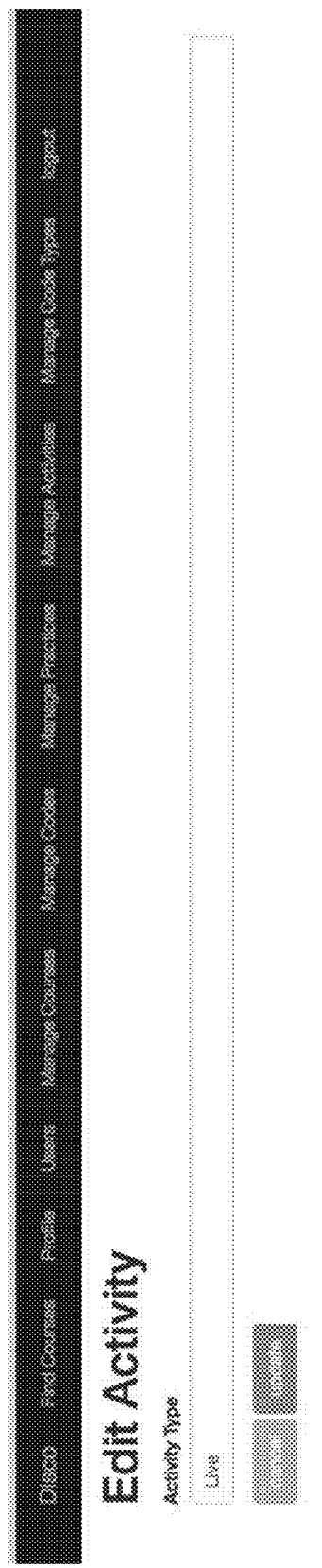

FIG. 22 illustrates an example user interface listing physician practices that are in the system portal. An administrator may access, view, and edit each entry in the practice list. FIG. 23 illustrates an example practice edit user interface that enables a user, such as an administrator, to edit a practice-type entry. FIG. 24 an example user interface enabling a user, such as an administrator, to view a list of the type of CME activities, and to edit or create the same. FIG. 25 illustrates an example user interface enabling a user, such as an administrator, to edit a CME activity type.

Figure 26:
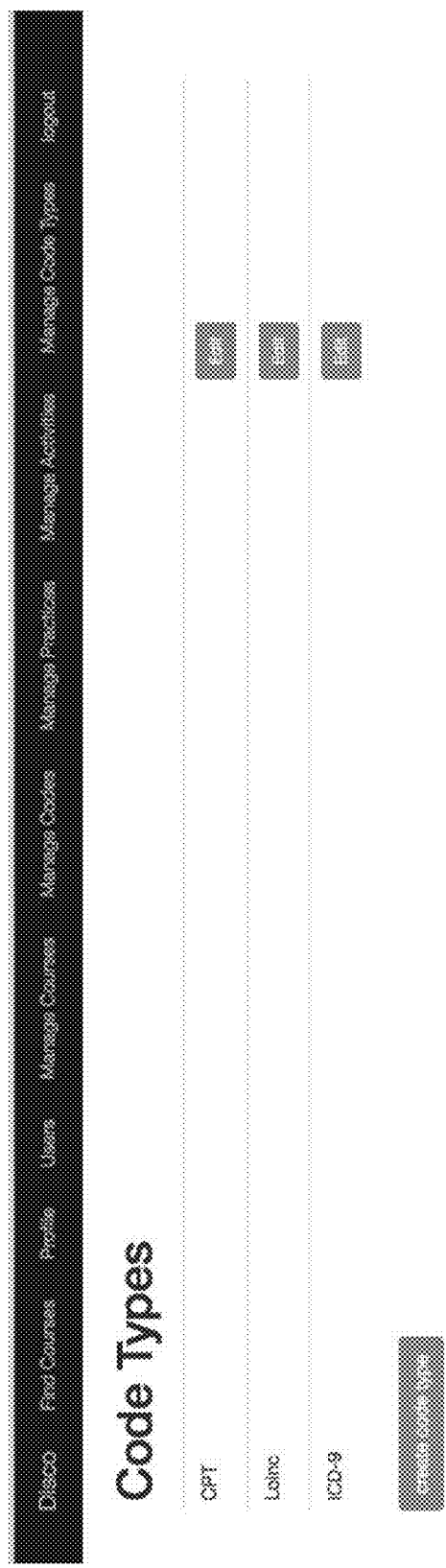
Figure 27:
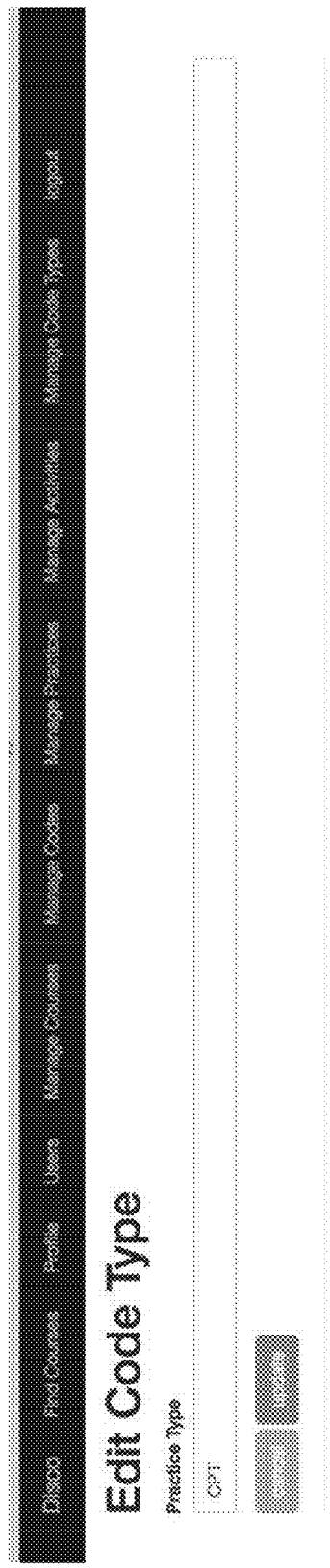

FIG. 26 illustrates an example user interface providing a list of the code types that are in the system portal, and associated edit controls. FIG. 27 illustrates an example user interface enabling a user, such as an administrator, to edit and update a code type that is in the system portal.

Thus, aspects of the present disclosure relate enabling course and program recommendations to be generated with high relevancy utilizing codes from an electronic medical records system. Optionally, such recommendations may be presented by the electronic medical records system.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The systems described herein may optionally include displays, user input devices (e.g., touchscreen, keyboard, mouse, voice recognition, etc.), network interfaces, etc.

The results of the disclosed methods may be stored in any type of computer data repository, such as relational databases and flat file systems that use volatile and/or non-volatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the phrase "click" may be used with respect to a user selecting a control, menu selection, or the like, other user inputs may be used, such as voice commands, text entry, gestures, etc. User inputs may, by way of example, be provided via an interface or in response to a prompt (e.g., a voice or text prompt). By way of example an interface may include text fields, wherein a user provides input by entering text into the field. By way of further example, a user input may be received via a menu selection (e.g., a drop down menu, a list or other arrangement via which the user can check via a check box or otherwise make a selection or selections, a group of individually selectable icons, a menu selection made via an interactive voice response system, etc.). When the user provides an input or activates a control, a corresponding computing system may perform a corresponding operation (e.g., store the user input, process the user input, provide a response to the user input, etc.). Some or all of the data, inputs and instructions provided by a user may optionally be stored in a system data store (e.g., a database), from which the system may access and retrieve such data, inputs, and instructions. The notifications and user interfaces described herein may be provided via a Web page, a dedicated or non-dedicated phone application, computer application, a short messaging service message (e.g., SMS, MMS, etc.), instant messaging, email, push notification, audibly, and/or otherwise.

The user terminals or devices described herein may be in the form of a mobile communication device (e.g., a cell phone, a VoIP equipped mobile device, etc.), laptop, tablet computer, interactive television, game console, media streaming device, head-wearable display, virtual reality display/headset, augmented reality display/headset, networked watch, etc. The user terminals may optionally include displays, user input devices (e.g., touchscreen, keyboard, mouse, voice recognition, etc.), network interfaces, etc.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

What is claimed is:

1. A system, comprising:
   a network interface;
   a computing system;
   nonvolatile memory that stores instructions configured to cause the computing system to:
   access a first set of nomenclature codes and respective code descriptions from at least a first data store;
   access, over a network using the network interface, course data for a first plurality of courses for medical service providers from at least a second data store;
   compare nomenclature code descriptions and course data;
   use the comparison of nomenclature code descriptions and course data to generate a mapping of courses to nomenclature codes in the first set of nomenclature codes;
   store the mapping of courses to nomenclature codes from the first set of nomenclature codes in a third data store;
   access, over a network using the network interface, nomenclature codes associated with patient records for a plurality of patients from an electronic medical record system associated with a medical service provider;
   determine with respect to the accessed patient records;
     a volume of nomenclature codes,
     a frequency of a given nomenclature code, and
     record dates of respective nomenclature codes;
   calculate relevancy values for respective nomenclature codes using the determined volume of nomenclature codes, frequency of the respective nomenclature code, record dates of the respective nomenclature code;
   access the stored mapping of courses to nomenclature codes;
   access a first set of preferences associated with the medical service provider;
   use the first set of preferences to generate a filtered set of courses from the first plurality of courses;
   use the calculated relevancy values, the accessed mapping of courses to nomenclature codes, and the filtered set of courses to generate a first ranked presentation of recommended courses;
   cause the first ranked presentation of recommended courses to be displayed via a user interface of the electronic medical record system associated with the medical service provider;
   detect, via data received over a network using the network interface, a course selection of a course included in the first ranked presentation of recommended courses by the medical service provider;
   use, by a learning engine, the detected selection to update learning engine weights;
   generate a second ranked presentation of recommended courses by the medical service provider using the learning engine with the updated learning engine weights.

2. The system as defined in claim 1, the operations further comprising:
   access program data for a first plurality of programs for patients;
   compare nomenclature code descriptions and program data;
   use the comparison of nomenclature code descriptions and program data to generate a mapping of programs to nomenclature codes;
   store the mapping of programs to nomenclature codes;
   access, over a network using the network interface, nomenclature codes associated with a record of a first patient from the electronic medical record system associated with the medical service provider;

identify nomenclature codes in the accessed records of the first patient;
access the stored mapping of programs to nomenclature codes;
use the identified nomenclature codes and the accessed mapping of programs to nomenclature codes to generate a first ranked presentation of recommended programs; and
cause the first ranked presentation of recommend programs to be displayed via a user interface of the electronic medical record system associated with the medical service provider.

3. The system as defined in claim 2, the operations further comprising:
cause the first ranked presentation of recommended programs to be presented in a user interface presenting the record of the first patient.

4. The system as defined in claim 2, the operations further comprising:
enable the medical service provider to select at least a first of the recommended programs;
enable the medical service provider to select a delivery mode of the selected first recommended program; and
cause the first recommended program to be delivered via a selected delivery mode.

5. The system as defined in claim 1, wherein the first ranked presentation of recommended courses is caused to be displayed with listings of recommended courses organized according to course type.

6. The system as defined in claim 1, the operations further comprising:
navigate the medical service provider from the displayed first ranked presentation of recommended courses to a source of a first course in response to the medical service provider course selection.

7. The system as defined in claim 1, the operations further comprising:
navigate the medical service provider from the displayed first ranked presentation of recommended courses to an enrollment user interface of a source of a first course in response to the medical service provider course selection.

8. The system as defined in claim 1, the operations further comprising:
access a second set of nomenclature codes and respective code descriptions from at least a first data store;
identify nomenclature codes in the first set of nomenclature codes that correspond to nomenclature codes in the second set of nomenclature codes; and
utilize the identification of nomenclature codes in the first set of nomenclature codes that correspond to nomenclature codes in the second set of nomenclature codes in the generation of the first ranked presentation of recommended courses.

9. The system as defined in claim 1, where the first set of preferences used to generate a filtered set of courses from the first plurality of courses comprises one or more preferred course types selected from a set of course types comprising:
an in-person course type;
a webinar course type;
a downloadable course type.

10. A system, comprising:
a network interface;
a computing system;
nonvolatile memory that stores instructions configured to cause the computing system to:
access a first set of codes and respective code descriptions from at least a first data store;
access, over a network using the network interface, course data for a first plurality of courses for medical service providers from at least a second data store;
compare code descriptions and course data;
use the comparison of code descriptions and course data to generate a mapping of courses to codes in the first set of codes;
store the mapping of courses to codes from the first set of codes in a third data store;
access, over a network using the network interface, codes associated with patient records for a plurality of patients from an electronic medical record system associated with a medical service provider;
identify codes in the accessed patient records for the plurality of patients;
calculate relevancy values for respective codes using the identified codes;
access the stored mapping of courses to codes;
use the calculated relevancy values and the accessed mapping of courses to codes to generate a first ranked presentation of recommended courses;
cause the first ranked presentation of recommended courses to be displayed via a user interface of the electronic medical record system associated with the medical service provider;
detect, via data received over a network using the network interface, a course selection of a course included in the first ranked presentation of recommended courses by the medical service provider; and
enable the medical service provider to enroll in the selected course.

11. The system as defined in claim 10, the operations further comprising:
access program data for a first plurality of programs for patients;
compare code descriptions and program data;
use the comparison of code descriptions and program data to generate a mapping of programs to codes;
store the mapping of programs to codes;
access, over a network using the network interface, codes associated with a record of a first patient from the electronic medical record system associated with the medical service provider;
identify codes in the accessed records of the first patient;
access the stored mapping of programs to codes;
use the identified codes and the accessed mapping of programs to codes to generate a first ranked presentation of recommended programs; and
cause the first ranked presentation of recommend programs to be displayed via a user interface of the electronic medical record system associated with the medical service provider.

12. The system as defined in claim 11, the operations further comprising:
cause the first ranked presentation of recommended programs to be presented in a user interface presenting the record of the first patient.

13. The system as defined in claim 11, the operations further comprising:
enable the medical service provider to select at least a first of the recommended programs;
enable the medical service provider to select a delivery mode of the selected first recommended program; and
cause the first recommended program to be delivered via a selected delivery mode.

14. The system as defined in claim 10, wherein the first ranked presentation of recommended courses is caused to be displayed with listings of recommended courses organized according to course type.

15. The system as defined in claim 10, the operations further comprising:
navigate the medical service provider from the displayed first ranked presentation of recommended courses to a source of a first course in response to the medical service provider course selection.

16. The system as defined in claim 10, the operations further comprising:
navigate the medical service provider from the displayed first ranked presentation of recommended courses to an enrollment user interface of a source of a first course in response to the medical service provider course selection.

17. The system as defined in claim 10, the operations further comprising:
access a second set of codes and respective code descriptions from at least a first data store;
identify codes in the first set of codes that correspond to codes in the second set of codes; and
utilize the identification of codes in the first set of codes that correspond to codes in the second set of codes in the generation of the first ranked presentation of recommended courses.

18. The system as defined in claim 10, where the first set of preferences used to generate a filtered set of courses from the first plurality of courses comprises one or more preferred course types selected from a set of course types comprising:
an in-person course type;
a webinar course type;
a downloadable course type.

19. The system as defined in claim 10, the operations further comprising:
build a weighted term vector for a given course, where a first type of content in the course data for a given course is weighted differently than a second type of content in the course data for the given course;
generate a query vector for a given code; and
rank query vectors for respective codes against a course term vector to determine a score.

20. The system as defined in claim 10, the operations further comprising:
receiving a token from a remote system indicating that the medical service provider completed a first course;
storing the token in memory;
transmitting the token over a network to certification authority system.

21. Nonvolatile media that stores instructions configured to cause the computing system to:
access a first set of codes and respective code descriptions from at least a first data store;
access course data for a first plurality of courses for medical service providers from at least a second data store;
compare code descriptions and course data;
use the comparison of code descriptions and course data to generate a mapping of courses to codes in the first set of codes;
store the mapping of courses to codes from the first set of codes in a third data store;
access codes associated with patient records for a plurality of patients from an electronic medical record system associated with a medical service provider;
identify codes in the accessed patient records for the plurality of patients;
calculate relevancy values for respective codes using the identified codes;
access the stored mapping of courses to codes;
use the calculated relevancy values and the accessed mapping of courses to codes to generate a first ranked presentation of recommended courses;
cause the first ranked presentation of recommended courses to be displayed via a user interface of the electronic medical record system associated with the medical service provider;
detect a course selection of a course included in the first ranked presentation of recommended courses by the medical service provider; and
enable the medical service provider to enroll in the selected course.

22. The medium as defined in claim 21, the operations further comprising:
access program data for a first plurality of programs for patients;
compare code descriptions and program data;
use the comparison of code descriptions and program data to generate a mapping of programs to codes;
store the mapping of programs to codes;
access, over a network using the network interface, codes associated with a record of a first patient from the electronic medical record system associated with the medical service provider;
identify codes in the accessed records of the first patient;
access the stored mapping of programs to codes;
use the identified codes and the accessed mapping of programs to codes to generate a first ranked presentation of recommended programs; and
cause the first ranked presentation of recommend programs to be displayed via a user interface of the electronic medical record system associated with the medical service provider.

23. The medium as defined in claim 21, the operations further comprising:
receiving a token from a remote system indicating that the medical service provider completed a first course;
storing the token in memory; and
transmitting an indication that the token was received over a network to certification authority system.

* * * * *

UNITED STATES PATENT AND TRADEMARK OFFICE
CERTIFICATE OF CORRECTION

PATENT NO. : 10,096,384 B2
APPLICATION NO. : 15/843813
DATED : October 9, 2018
INVENTOR(S) : John W. Eastman Page 1 of 1

It is certified that error appears in the above-identified patent and that said Letters Patent is hereby corrected as shown below:

In the Drawings

On Sheet 8 of 28 (FIG. 7), Line 9: Change "HYPERTENTION" to --HYPERTENSION--.

On Sheet 8 of 28 (FIG. 7), Line 14: Change "PROCEDINGS" to --PROCEEDINGS--.

On Sheet 8 of 28 (FIG. 7), Line 16: Change "CORDIOLOGY" to --CARDIOLOGY--.

On Sheet 10 of 28 (FIG. 9), Line 12: Change "HYPERTENTION" to --HYPERTENSION--.

In the Specification

On Column 4, Line 23: Change "SNOWMED" to --SNOMED--.

On Column 6, Line 42: Change "SNOWMED," to --SNOMED,--.

On Column 7, Line 11: Change "SNOWMED," to --SNOMED,--.

On Column 14, Line 40: Change "SNOWMED," to --SNOMED--.

In the Claims

On Column 27, Lines 51-52: In Claim 21, change "Nonvolatile media that stores instructions configured to cause the computing system to:" to --A nonvolatile computer readable medium that stores instructions configured to cause a computing system to perform operations comprising:--.

Signed and Sealed this
Fifth Day of February, 2019

Andrei Iancu
*Director of the United States Patent and Trademark Office*